(12) United States Patent
Pang et al.

(10) Patent No.: US 9,623,174 B2
(45) Date of Patent: *Apr. 18, 2017

(54) IMPLANTABLE PUMPS AND CANNULAS THEREFOR

(75) Inventors: Changlin Pang, Pasadena, CA (US);
Jason Shih, Yorba Linda, CA (US);
Fukang Jiang, Pasadena, CA (US);
Sean Caffey, Manhattan Beach, CA (US); Mark Humayun, Glendale, CA (US); Yu-Chong Tai, Pasadena, CA (US)

(73) Assignee: MINIPUMPS, LLC, Manhattan Beach, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/463,265

(22) Filed: May 8, 2009

(65) Prior Publication Data
US 2009/0306585 A1 Dec. 10, 2009

Related U.S. Application Data

(60) Provisional application No. 61/051,422, filed on May 8, 2008, provisional application No. 61/197,769, filed
(Continued)

(51) Int. Cl.
*A61M 5/155* (2006.01)
*A61M 5/168* (2006.01)
(Continued)

(52) U.S. Cl.
CPC ........ *A61M 5/14276* (2013.01); *A61M 5/148* (2013.01); *A61M 5/16804* (2013.01);
(Continued)

(58) Field of Classification Search
CPC .............. A61M 5/14276; A61M 5/148; A61M 5/16804; A61M 5/16854;
(Continued)

(56) References Cited

U.S. PATENT DOCUMENTS

| 2,445,477 A | 7/1948 | Folkman |
| 3,175,558 A | 3/1965 | Caillonette et al. |

(Continued)

FOREIGN PATENT DOCUMENTS

| CN | 1321096 A | 11/2001 |
| CN | 102576385 A | 7/2012 |

(Continued)

OTHER PUBLICATIONS

Invitation to Pay Additional Fees and Partial International Search for PCT Application No. PCT/US2009/043317, mailed Nov. 16, 2009, 5 pages.

(Continued)

*Primary Examiner* — Bhisma Mehta
*Assistant Examiner* — Jenna Zhang
(74) *Attorney, Agent, or Firm* — Morgan, Lewis & Bockius LLP

(57) ABSTRACT

In various embodiments, an implantable pump includes a cannula. The pump (e.g., the cannula thereof) may include, for example, flow sensors, pressure sensors, filters, and/or other components.

27 Claims, 14 Drawing Sheets

Related U.S. Application Data on Oct. 30, 2008, provisional application No. 61/197,751, filed on Oct. 30, 2008, provisional application No. 61/198,090, filed on Nov. 3, 2008, provisional application No. 61/198,131, filed on Nov. 3, 2008.

(51) Int. Cl.
*A61M 5/142* (2006.01)
*A61M 5/148* (2006.01)
*A61F 9/00* (2006.01)
*A61M 5/14* (2006.01)
*A61F 9/007* (2006.01)

(52) U.S. Cl.
CPC ...... *A61F 9/00781* (2013.01); *A61M 5/16854* (2013.01); *A61M 2005/14204* (2013.01); *A61M 2205/3331* (2013.01); *A61M 2205/3368* (2013.01); *A61M 2210/0612* (2013.01); *A61M 2210/0693* (2013.01)

(58) Field of Classification Search
CPC .. A61M 2205/3368; A61M 2205/3331; A61M 2210/0693; A61M 2210/0612
USPC .................................. 604/891.1, 890.1, 67
See application file for complete search history.

(56) References Cited

U.S. PATENT DOCUMENTS

| | | | |
|---|---|---|---|
| 3,731,681 A | 5/1973 | Blackshear et al. | |
| 3,760,805 A | 9/1973 | Higuchi | |
| 3,894,538 A | 7/1975 | Richter | |
| 3,916,899 A | 11/1975 | Theeuwes et al. | |
| 3,977,404 A | 8/1976 | Theeuwes | |
| 4,140,121 A | 2/1979 | Kuhl et al. | |
| 4,140,122 A | 2/1979 | Kuhl et al. | |
| 4,150,673 A | 4/1979 | Watt | |
| 4,164,560 A | 8/1979 | Folkman et al. | |
| 4,180,375 A | 12/1979 | Magnussen | |
| 4,203,441 A | 5/1980 | Theeuwes | |
| 4,237,881 A | 12/1980 | Beigler et al. | |
| 4,300,554 A | 11/1981 | Hessberg et al. | |
| 4,373,527 A | 2/1983 | Fischell | |
| 4,543,088 A | 9/1985 | Bootman et al. | |
| 4,553,973 A | 11/1985 | Edgren | |
| 4,692,145 A | 9/1987 | Weyant | |
| 4,738,657 A | 4/1988 | Hancock et al. | |
| 4,751,926 A | 6/1988 | Sasaki | |
| 4,760,837 A | 8/1988 | Petit | |
| 4,781,675 A | 11/1988 | White | |
| 4,781,695 A | 11/1988 | Dalton | |
| 4,838,887 A | 6/1989 | Idriss | |
| 4,853,224 A | 8/1989 | Wong | |
| 4,886,499 A | 12/1989 | Cirelli et al. | |
| 4,886,514 A | 12/1989 | Maget | |
| 4,888,176 A | 12/1989 | Langer et al. | |
| 4,902,278 A | 2/1990 | Maget et al. | |
| 4,923,457 A | 5/1990 | Ellingsen | |
| 4,944,659 A | 7/1990 | Labbe et al. | |
| 4,959,217 A | 9/1990 | Sanders et al. | |
| 4,969,874 A | 11/1990 | Michel et al. | |
| 5,062,834 A | 11/1991 | Gross et al. | |
| 5,066,276 A * | 11/1991 | Wang | A61F 9/00736 604/121 |
| 5,067,491 A * | 11/1991 | Taylor, II | A61B 5/0215 600/486 |
| 5,090,963 A | 2/1992 | Gross et al. | |
| 5,108,372 A * | 4/1992 | Swenson | A61M 5/16886 604/113 |
| 5,135,498 A | 8/1992 | Kam et al. | |
| 5,135,499 A | 8/1992 | Tafani et al. | |
| 5,147,647 A | 9/1992 | Darougar | |
| 5,163,909 A | 11/1992 | Stewart | |
| 5,164,188 A | 11/1992 | Wong | |
| 5,171,213 A | 12/1992 | Price, Jr. | |
| 5,178,604 A | 1/1993 | Baerveldt et al. | |
| 5,207,227 A * | 5/1993 | Powers | A61B 5/028 600/488 |
| 5,213,568 A | 5/1993 | Lattin et al. | |
| 5,242,406 A | 9/1993 | Gross et al. | |
| 5,242,408 A | 9/1993 | Jhuboo et al. | |
| 5,252,192 A | 10/1993 | Ludwig | |
| 5,279,607 A | 1/1994 | Schentag et al. | |
| 5,318,540 A | 6/1994 | Athayde et al. | |
| 5,318,557 A | 6/1994 | Gross | |
| 5,354,264 A | 10/1994 | Bae et al. | |
| 5,368,571 A | 11/1994 | Horres, Jr. | |
| 5,399,166 A | 3/1995 | Laing | |
| 5,407,441 A | 4/1995 | Greenbaum | |
| 5,425,716 A | 6/1995 | Kawasaki et al. | |
| 5,443,505 A | 8/1995 | Wong et al. | |
| 5,458,095 A | 10/1995 | Post et al. | |
| 5,462,739 A | 10/1995 | Dan et al. | |
| 5,472,436 A | 12/1995 | Fremstad | |
| 5,474,527 A | 12/1995 | Bettinger | |
| 5,476,445 A | 12/1995 | Baerveldt et al. | |
| 5,505,697 A | 4/1996 | McKinnon et al. | |
| 5,527,288 A | 6/1996 | Gross et al. | |
| 5,553,741 A | 9/1996 | Sancoff et al. | |
| 5,616,219 A | 4/1997 | Patterson | |
| 5,629,008 A | 5/1997 | Lee | |
| 5,676,651 A | 10/1997 | Larson, Jr. et al. | |
| 5,697,153 A | 12/1997 | Saaski et al. | |
| 5,704,520 A | 1/1998 | Gross et al. | |
| 5,707,499 A | 1/1998 | Joshi et al. | |
| 5,713,857 A | 2/1998 | Grimard et al. | |
| 5,725,017 A | 3/1998 | Elsberry et al. | |
| 5,725,493 A | 3/1998 | Avery et al. | |
| 5,741,275 A | 4/1998 | Wyssmann | |
| 5,782,799 A | 7/1998 | Jacobsen et al. | |
| 5,785,688 A | 7/1998 | Joshi et al. | |
| 5,788,682 A | 8/1998 | Maget | |
| 5,798,114 A | 8/1998 | Elsberry et al. | |
| 5,798,115 A | 8/1998 | Santerre et al. | |
| 5,800,420 A * | 9/1998 | Gross | A61K 9/0021 204/280 |
| 5,824,072 A | 10/1998 | Wong | |
| 5,830,173 A | 11/1998 | Avery et al. | |
| 5,836,935 A | 11/1998 | Ashton et al. | |
| 5,868,697 A | 2/1999 | Richter et al. | |
| 5,891,097 A * | 4/1999 | Saito | A61M 5/1483 604/131 |
| 5,904,144 A | 5/1999 | Hammang et al. | |
| 5,951,538 A | 9/1999 | Joshi et al. | |
| 5,989,579 A | 11/1999 | Darougar et al. | |
| 5,993,374 A | 11/1999 | Kick | |
| 5,993,414 A | 11/1999 | Haller | |
| 6,048,328 A | 4/2000 | Haller et al. | |
| 6,129,696 A | 10/2000 | Sibalis | |
| 6,144,106 A | 11/2000 | Bearinger et al. | |
| 6,203,523 B1 | 3/2001 | Haller et al. | |
| 6,240,962 B1 | 6/2001 | Tai et al. | |
| 6,251,090 B1 | 6/2001 | Avery et al. | |
| 6,254,586 B1 | 7/2001 | Mann et al. | |
| 6,264,971 B1 | 7/2001 | Darougar et al. | |
| 6,281,192 B1 | 8/2001 | Leahy et al. | |
| 6,287,295 B1 | 9/2001 | Chen et al. | |
| 6,370,970 B1 | 4/2002 | Hosokawa et al. | |
| 6,375,972 B1 | 4/2002 | Guo et al. | |
| 6,390,791 B1 | 5/2002 | Maillefer et al. | |
| 6,408,878 B2 | 6/2002 | Unger et al. | |
| 6,413,238 B1 | 7/2002 | Maget | |
| 6,416,777 B1 | 7/2002 | Yaacobi | |
| 6,458,102 B1 * | 10/2002 | Mann | A61M 5/14593 222/399 |
| 6,491,684 B1 | 12/2002 | Joshi et al. | |
| 6,520,936 B1 * | 2/2003 | Mann | A61M 5/14276 604/141 |
| 6,527,744 B1 | 3/2003 | Kriesel et al. | |
| 6,537,268 B1 | 3/2003 | Gibson et al. | |
| 6,589,205 B1 | 7/2003 | Meadows | |
| 6,669,950 B2 | 12/2003 | Yaacobi | |
| 6,697,694 B2 | 2/2004 | Mogensen | |

(56) References Cited

U.S. PATENT DOCUMENTS

| | | | |
|---|---|---|---|
| 6,699,394 B2 | 3/2004 | Tai et al. | |
| 6,713,081 B2 | 3/2004 | Robinson et al. | |
| 6,719,750 B2 | 4/2004 | Varner et al. | |
| 6,817,252 B2 | 11/2004 | Wiklund et al. | |
| 6,852,097 B1 | 2/2005 | Fulton, III | |
| 6,852,106 B2 | 2/2005 | Watson et al. | |
| 6,899,137 B2 | 5/2005 | Unger et al. | |
| 6,948,918 B2 | 9/2005 | Hansen | |
| 6,955,670 B2 | 10/2005 | Martin et al. | |
| 6,973,718 B2 * | 12/2005 | Sheppard, Jr. | A61K 9/0009 29/841 |
| 7,070,577 B1 | 7/2006 | Haller et al. | |
| 7,225,683 B2 * | 6/2007 | Harnett | G01F 1/7088 73/861.12 |
| 7,276,050 B2 | 10/2007 | Franklin | |
| 7,351,303 B2 | 4/2008 | Liu et al. | |
| 7,429,258 B2 | 9/2008 | Angel et al. | |
| 7,470,267 B2 | 12/2008 | Joshi et al. | |
| 7,517,440 B2 | 4/2009 | Anex et al. | |
| 7,524,304 B2 | 4/2009 | Genosar | |
| 7,537,590 B2 | 5/2009 | Santini, Jr. et al. | |
| 7,544,190 B2 | 6/2009 | Pickup et al. | |
| 7,606,615 B2 | 10/2009 | Makower et al. | |
| 7,766,873 B2 | 8/2010 | Moberg et al. | |
| 7,828,771 B2 | 11/2010 | Chiang et al. | |
| 7,867,203 B2 | 1/2011 | Rosenberg et al. | |
| 7,887,508 B2 | 2/2011 | Meng et al. | |
| 7,931,643 B2 | 4/2011 | Olsen et al. | |
| 8,147,447 B2 | 4/2012 | Sundar et al. | |
| 8,231,609 B2 | 7/2012 | Pang et al. | |
| 8,285,328 B2 | 10/2012 | Caffey et al. | |
| 8,585,648 B2 | 11/2013 | Caffey | |
| 8,920,376 B2 | 12/2014 | Caffey et al. | |
| 8,939,930 B2 | 1/2015 | Li et al. | |
| 2002/0016569 A1 | 2/2002 | Critchlow et al. | |
| 2002/0026176 A1 | 2/2002 | Varner et al. | |
| 2002/0040208 A1 | 4/2002 | Flaherty et al. | |
| 2002/0103412 A1 | 8/2002 | Trimmer | |
| 2002/0156462 A1 | 10/2002 | Stultz | |
| 2002/0188282 A1 | 12/2002 | Greenberg | |
| 2003/0014014 A1 | 1/2003 | Nitzan | |
| 2003/0014036 A1 | 1/2003 | Varner et al. | |
| 2003/0064088 A1 | 4/2003 | Carvalho et al. | |
| 2003/0069560 A1 | 4/2003 | Adamis et al. | |
| 2003/0141618 A1 | 7/2003 | Braithwaite et al. | |
| 2004/0028655 A1 | 2/2004 | Nelson et al. | |
| 2004/0096410 A1 | 5/2004 | Maley et al. | |
| 2004/0100528 A1 | 5/2004 | Howkins et al. | |
| 2004/0106914 A1 | 6/2004 | Coppeta et al. | |
| 2004/0126253 A1 | 7/2004 | Gray et al. | |
| 2004/0143221 A1 | 7/2004 | Shadduck | |
| 2004/0175410 A1 | 9/2004 | Ashton et al. | |
| 2004/0188648 A1 | 9/2004 | Xie et al. | |
| 2004/0199130 A1 | 10/2004 | Chornenky et al. | |
| 2004/0208910 A1 | 10/2004 | Ashton et al. | |
| 2004/0228734 A1 | 11/2004 | Jeon et al. | |
| 2005/0010175 A1 | 1/2005 | Beedon et al. | |
| 2005/0065500 A1 | 3/2005 | Couvillon et al. | |
| 2005/0076242 A1 | 4/2005 | Breuer | |
| 2005/0096707 A1 | 5/2005 | Hill et al. | |
| 2005/0106225 A1 | 5/2005 | Massengale et al. | |
| 2005/0175708 A1 | 8/2005 | Carrasquillo et al. | |
| 2005/0187515 A1 | 8/2005 | Varrichio et al. | |
| 2005/0208103 A1 | 9/2005 | Adamis et al. | |
| 2005/0209562 A1 | 9/2005 | Kim | |
| 2005/0214129 A1 | 9/2005 | Greene et al. | |
| 2006/0004330 A1 | 1/2006 | Carlisle et al. | |
| 2006/0012280 A1 | 1/2006 | Kang et al. | |
| 2006/0014793 A1 | 1/2006 | Nakamura et al. | |
| 2006/0047538 A1 | 3/2006 | Condurso et al. | |
| 2006/0052666 A1 | 3/2006 | Kumar et al. | |
| 2006/0052768 A1 | 3/2006 | Joshi et al. | |
| 2006/0075016 A1 | 4/2006 | Kanayama et al. | |
| 2006/0089619 A1 | 4/2006 | Ginggen | |
| 2006/0116641 A1 * | 6/2006 | Gordon | A61K 9/0004 604/141 |
| 2006/0167435 A1 | 7/2006 | Adamis et al. | |
| 2006/0178655 A1 | 8/2006 | Santini et al. | |
| 2006/0200073 A1 | 9/2006 | Radmer et al. | |
| 2006/0200097 A1 | 9/2006 | Humayun et al. | |
| 2006/0258994 A1 | 11/2006 | Avery | |
| 2006/0259015 A1 | 11/2006 | Steinbach | |
| 2006/0271020 A1 | 11/2006 | Huang et al. | |
| 2007/0021735 A1 | 1/2007 | Bhavaraju et al. | |
| 2007/0060870 A1 | 3/2007 | Tolle et al. | |
| 2007/0066939 A1 | 3/2007 | Krulevitch et al. | |
| 2007/0084765 A1 | 4/2007 | Tse | |
| 2007/0093752 A1 | 4/2007 | Zhao et al. | |
| 2007/0106199 A1 | 5/2007 | Krivoy et al. | |
| 2007/0106218 A1 | 5/2007 | Yodfat et al. | |
| 2007/0106557 A1 | 5/2007 | Varghese | |
| 2007/0112328 A1 | 5/2007 | Steinbach et al. | |
| 2007/0118066 A1 | 5/2007 | Pinchuk et al. | |
| 2007/0173900 A1 | 7/2007 | Siegel et al. | |
| 2007/0191770 A1 | 8/2007 | Moberg et al. | |
| 2007/0228071 A1 * | 10/2007 | Kamen | G05D 7/0647 222/52 |
| 2007/0255233 A1 | 11/2007 | Haase | |
| 2007/0255235 A1 | 11/2007 | Olsen et al. | |
| 2007/0255250 A1 | 11/2007 | Moberg et al. | |
| 2007/0255261 A1 | 11/2007 | Haase | |
| 2007/0269487 A1 | 11/2007 | de Juan et al. | |
| 2007/0275384 A1 | 11/2007 | Leppert et al. | |
| 2008/0015494 A1 | 1/2008 | Santini et al. | |
| 2008/0022789 A1 | 1/2008 | Okuno et al. | |
| 2008/0033255 A1 | 2/2008 | Essenpreis et al. | |
| 2008/0039768 A1 | 2/2008 | Francis | |
| 2008/0039792 A1 * | 2/2008 | Meng | A61K 9/0024 604/114 |
| 2008/0097412 A1 | 4/2008 | Shuros et al. | |
| 2008/0102119 A1 | 5/2008 | Grovender et al. | |
| 2008/0119707 A1 | 5/2008 | Stafford | |
| 2008/0125702 A1 | 5/2008 | Blischak et al. | |
| 2008/0170936 A1 | 7/2008 | Den Toonder et al. | |
| 2008/0181930 A1 | 7/2008 | Rodstrom et al. | |
| 2008/0194053 A1 | 8/2008 | Huang | |
| 2008/0234637 A1 | 9/2008 | McConnell et al. | |
| 2008/0243071 A1 | 10/2008 | Quijano et al. | |
| 2008/0269664 A1 | 10/2008 | Trovato et al. | |
| 2008/0275384 A1 | 11/2008 | Mastrototaro | |
| 2008/0312584 A1 | 12/2008 | Montgomery et al. | |
| 2009/0028824 A1 | 1/2009 | Chiang et al. | |
| 2009/0041624 A1 | 2/2009 | Hochmuth et al. | |
| 2009/0112188 A1 | 4/2009 | Santini, Jr. et al. | |
| 2009/0188576 A1 | 7/2009 | Kang et al. | |
| 2009/0192493 A1 | 7/2009 | Meng et al. | |
| 2009/0205399 A1 | 8/2009 | Sun et al. | |
| 2009/0227855 A1 | 9/2009 | Hill et al. | |
| 2009/0234366 A1 | 9/2009 | Tsai et al. | |
| 2009/0234594 A1 | 9/2009 | Carlisle et al. | |
| 2009/0240215 A1 | 9/2009 | Humayun et al. | |
| 2009/0259176 A1 | 10/2009 | Yairi | |
| 2009/0281528 A1 | 11/2009 | Grovender et al. | |
| 2009/0306594 A1 | 12/2009 | Pang et al. | |
| 2009/0306595 A1 | 12/2009 | Shih et al. | |
| 2009/0306633 A1 | 12/2009 | Trovato et al. | |
| 2009/0308752 A1 | 12/2009 | Evans et al. | |
| 2009/0311133 A1 | 12/2009 | Pang et al. | |
| 2009/0312742 A1 | 12/2009 | Pang et al. | |
| 2010/0004639 A1 | 1/2010 | Pang et al. | |
| 2010/0030550 A1 | 2/2010 | Travieso et al. | |
| 2010/0049120 A1 | 2/2010 | Dijksman et al. | |
| 2010/0101670 A1 | 4/2010 | Juncker et al. | |
| 2010/0114002 A1 | 5/2010 | O'Mahony et al. | |
| 2010/0143448 A1 | 6/2010 | Nisato et al. | |
| 2010/0222769 A1 | 9/2010 | Meng et al. | |
| 2010/0234805 A1 | 9/2010 | Kaufmann et al. | |
| 2010/0241103 A1 | 9/2010 | Kraft et al. | |
| 2010/0292557 A1 | 11/2010 | Pesach et al. | |
| 2010/0292635 A1 | 11/2010 | Sundar | |
| 2010/0305550 A1 | 12/2010 | Meng et al. | |
| 2011/0144586 A1 | 6/2011 | Michaud et al. | |
| 2011/0184342 A1 | 7/2011 | Pesach et al. | |

(56) References Cited

U.S. PATENT DOCUMENTS

| | | |
|---|---|---|
| 2011/0190702 A1 | 8/2011 | Stumber |
| 2011/0202032 A1 | 8/2011 | Shih et al. |
| 2011/0270188 A1 | 11/2011 | Caffey et al. |
| 2011/0275410 A1 | 11/2011 | Caffey et al. |
| 2011/0275987 A1 | 11/2011 | Caffey et al. |
| 2012/0041427 A1 | 2/2012 | Caffey et al. |
| 2012/0046651 A1 | 2/2012 | Beyer et al. |
| 2012/0222488 A1 | 9/2012 | Slocum |
| 2012/0283691 A1 | 11/2012 | Barnes et al. |
| 2013/0178792 A1 | 7/2013 | Li |
| 2013/0178826 A1 | 7/2013 | Li |
| 2013/0184640 A1 | 7/2013 | Li |
| 2013/0184641 A1 | 7/2013 | Li |
| 2013/0276974 A1 | 10/2013 | Pang et al. |
| 2013/0289497 A1 | 10/2013 | Humayun et al. |
| 2013/0296810 A1 | 11/2013 | Humayun et al. |
| 2014/0074058 A1 | 3/2014 | Shih et al. |
| 2014/0088554 A1 | 3/2014 | Li et al. |
| 2014/0088555 A1 | 3/2014 | Li et al. |
| 2014/0094770 A1 | 4/2014 | Li et al. |
| 2014/0094771 A1 | 4/2014 | Li et al. |

FOREIGN PATENT DOCUMENTS

| | | |
|---|---|---|
| CN | 103108665 A | 5/2013 |
| CN | 102202719 B | 11/2014 |
| CN | 104353150 A | 2/2015 |
| DE | 3915708 | 2/1990 |
| DE | 4436540 A1 | 4/1996 |
| DE | 102004036358 A1 | 2/2006 |
| EP | 209677 A1 | 1/1987 |
| EP | 0251680 | 1/1988 |
| EP | 646381 A1 | 4/1995 |
| EP | 815896 A2 | 1/1998 |
| EP | 1649884 A1 | 4/2006 |
| EP | 1841491 A1 | 10/2007 |
| EP | 2467797 A1 | 6/2012 |
| EP | 2780055 A2 | 9/2014 |
| EP | 2320989 B1 | 3/2015 |
| GB | 1345764 | 2/1974 |
| GB | 1452104 A | 10/1976 |
| IE | 38474 | 3/1978 |
| JP | 2003-299732 A | 10/2003 |
| JP | 2015-502785 A | 1/2015 |
| WO | 84/01718 A1 | 5/1984 |
| WO | 86/07269 A1 | 12/1986 |
| WO | WO-95/13838 | 5/1995 |
| WO | 96/41159 A1 | 12/1996 |
| WO | WO-99/17749 | 4/1999 |
| WO | WO-99/38552 | 8/1999 |
| WO | WO-99/62576 | 12/1999 |
| WO | WO-00/26367 | 5/2000 |
| WO | WO-00/40089 | 7/2000 |
| WO | 00/72900 A1 | 12/2000 |
| WO | 00/74751 A1 | 12/2000 |
| WO | WO-01/12158 | 2/2001 |
| WO | 01/21234 A1 | 3/2001 |
| WO | 01/26706 A2 | 4/2001 |
| WO | WO-01/56634 | 8/2001 |
| WO | WO-01/66173 | 9/2001 |
| WO | WO-01/94784 | 12/2001 |
| WO | 02/40083 A2 | 5/2002 |
| WO | 02/067688 A1 | 9/2002 |
| WO | WO-03/002170 | 1/2003 |
| WO | 03/009774 A2 | 2/2003 |
| WO | WO-03/024360 | 3/2003 |
| WO | 03/072193 A1 | 9/2003 |
| WO | 03/090509 A2 | 11/2003 |
| WO | 2004/002878 A2 | 1/2004 |
| WO | WO-2004/014969 | 2/2004 |
| WO | 2004/026281 A2 | 4/2004 |
| WO | 2004/067066 A1 | 8/2004 |
| WO | WO-2004/066871 | 8/2004 |
| WO | WO-2004/073551 | 9/2004 |
| WO | 2005/034814 A1 | 4/2005 |
| WO | WO-2005/046769 | 5/2005 |
| WO | WO-2006/012280 | 2/2006 |
| WO | WO-2006/014793 | 2/2006 |
| WO | 2006/026768 A1 | 3/2006 |
| WO | 2006/060586 A1 | 6/2006 |
| WO | WO-2006/075016 | 7/2006 |
| WO | 2006/121921 A2 | 11/2006 |
| WO | 2007/035621 A1 | 3/2007 |
| WO | 2007/065944 A1 | 6/2007 |
| WO | WO-2007/084765 | 7/2007 |
| WO | WO-2007/106557 | 9/2007 |
| WO | 2007/112328 A2 | 10/2007 |
| WO | 2007/125456 A2 | 11/2007 |
| WO | 2007/138590 A2 | 12/2007 |
| WO | 2008/024808 A2 | 2/2008 |
| WO | 2008/054788 A2 | 5/2008 |
| WO | 2008/139460 A2 | 11/2008 |
| WO | 2008/151667 A1 | 12/2008 |
| WO | 2009/015389 A2 | 1/2009 |
| WO | 2009/048144 A1 | 4/2009 |
| WO | 2009/086112 A2 | 7/2009 |
| WO | 2009/137780 A2 | 11/2009 |
| WO | 2011/022484 A1 | 2/2011 |
| WO | 2011/025913 A1 | 3/2011 |
| WO | 2011/028997 A1 | 3/2011 |
| WO | 2011/133724 A2 | 10/2011 |
| WO | 2011/133724 A3 | 1/2012 |
| WO | 2013/075109 A2 | 5/2013 |
| WO | 2013/075109 A9 | 7/2013 |
| WO | 2013/075109 A3 | 10/2013 |
| WO | 2014/047638 A1 | 3/2014 |
| WO | 2014/047657 A2 | 3/2014 |
| WO | 2014/047657 A3 | 7/2014 |
| WO | 2015/048093 A2 | 4/2015 |

OTHER PUBLICATIONS

Invitation to Pay Additional Fees and Partial International Search for PCT Application No. PCT/US2009/043313, mailed Nov. 16, 2009, 6 pages.

International Search Report for PCT Application No. PCT/US2009/043325, mailed Dec. 11, 2009, 9 pages.

Written Opinion for PCT Application No. PCT/US2009/043325, mailed Dec. 11, 2009, 9 pages.

Examination Report for European Patent Application No. 07753177.0, mailed Feb. 5, 2010, 3 pages.

International Search Report for PCT Application No. PCT/US2009/043317, mailed Feb. 16, 2010, 7 pages.

Written Opinion for PCT Application No. PCT/US2009/043317, mailed Feb. 16, 2010, 8 pages.

International Search Report for PCT Application No. PCT/US2009/043313, mailed Feb. 25, 2010, 8 pages.

Written Opinion for PCT Application No. PCT/US2009/043313, mailed Feb. 25, 2010, 8 pages.

"FDA Approves and Industry FIRST!—The MED-EL Cochlear Implant System in FDA Approved for Use With Magnetic Resonance Imaging (MRI)," PR Newswire, Durham, N.C., Jun. 18, 2003, 3 pages.

"Krupin Eye Valve with Scleral Buckle, Krupin Eye Valve With Disk," Hood Laboratories Catalogue, F 079 Rev. Nov. 1992, 4 pages.

"The Optimed Advantage—Glaucoma Pressure Regulator," Optimed Advertising Brochure, Journal of Glaucoma, vol. 2, No. 3, 1993, 4 pages.

Chen et al. "Floating-Disk Parylene Micro Check Valve," Micro Electro Mechanical Systems, 2007, IEEE 20th International Conference on MEMS, Jan. 21-25, 2007, 4 pages.

Chen et al. "Floating-Disk Parylene Microvalve for Self-Regulating Biomedical Flow Controls," IEEE 21st International Conference on MEMS, 2008, Jan. 13-17, 2008, 4 pages.

Chen et al. "Surface-Micromachined Parylene Dual Valves for On-Chip Unpowered Microflow Regulation," Journal of Microelectromechanical Systems, vol. 16, No. 2, Apr. 2007, pp. 223-231.

(56) References Cited

OTHER PUBLICATIONS

Choudhri et al. "A Comparison of Dorzolamide-Timolol Combination Versus the Concomitant Drugs," American Journal of Ophthalmology, Dec. 2000, 130, pp. 832-833.
Eliason et al. "An Ocular Perfusion System," Invest. Ophthalmol. Vis. Sci., vol. 19, No. 1, Jan. 1980, pp. 102-105.
Hashizoe et al. "Scleral Plug of Biodegradable Polymers for Controlled Release in the Vitreous" Arch Ophthalmol, vol. 112, Oct. 1994, pp. 1380-1384.
Jabs "Treatment of Cytomegalovirus Retinitis—1992," Arch Ophthlmol, vol. 110, Feb. 1992, pp. 185-187.
Khouri et al. "Use of Fixed-Dose Combination Drugs for the Treatment of Glaucoma," Drugs Aging, 2007, 24, 12, pp. 1007-1016.
Kimura et al. "A New Vitreal Drug Delivery System Using an Implantable Biodegradable Polymeric Device," Investigative Ophthalmology & Visual Science, May 1994, vol. 35, No. 6; pp. 2815-2819.
Lo et al. "A Refillable Polymer Drug Delivery Device for Treatment of Ocular Diseases," The Royal Society of Chemistry, Jan. 1, 2007, 28 pages.
Michelson et al. "Experimental Endophtalmitis Treated With an Implantable Osmotic Minipump," Arch Ophthalmol, vol. 97, Jul. 1979, pp. 1345-1346.
Miki, et al. "A Method for Chronic Drug Infusion Into the Eye," Japanese Journal of Ophthalmology, vol. 28, 1984, pp. 140-146.
Pincus et al. "Why are Only 50% of Courses of Anti-Tumor Necrosis Factor Agents Continued for Only 2 Years in Some Settings? Need for Longterm Observations in Standard Care to Compliment Clinical Trials," Journal of Rheumatology, 2006, 33, 12, pp. 2372-2375.
Pope et al. "MRI in Patients with High-Grade Gliomas Treated with Bevacizumab and Chemotherapy," Neurology, 2006, 66, pp. 1258-1260.
Rubsamen et al. "Prevention of Experimental Proliferative Vitreoretinopathy With a Biodegradable Intravitreal Implant for the Sustained Release of Fluorouracil," Arch Ophthalmol, vol. 112, Mar. 1994, pp. 407-413.
Sanborn et al. "Sustained-Release Ganciclovir Therapy for Treatment of Cytomegalovirus Retinitis," Arch Ophthmol, vol. 110, Feb. 1992; pp. 188-195.
Smith et al. "Intravitreal Sustained-Release Ganiclovir," Arch Ophthlmol, vol. 110, Feb. 1992, pp. 255-258.
Stark-Vance, "Bevacizumab and CPT-11 in the Treatment of Relapsed Malignant Glioma," Abstract from the World Federation of Neuro-Oncology Second Quadrennial Meeting and Sixth Meeting of the European Association for Neuro-Oncology, May 5-8, 2005, Abstract 342, p. 369.
Steyer "Alcon Eye-Drug Setback Raises the Stakes," The Street. Com, Oct. 14, 2004, 4 pages.
Strohmaier et al. "The Efficacy and Safety of the Dorzolamide-Timolol Combination Versus the Concomitant Administration of its Components," Ophthalmology, Oct. 1998, vol. 105, No. 10, pp. 1936-1944.
Xie et al. "An Electrochemical Pumping System for On-Chip Gradient Generation," Analytical Chemistry, 8 pages (A-H).
Examination Report for European Patent Application No. 07753177.0, mailed Jan. 29, 2009, 6 pages.
Invitation to Pay Additional Fees and Partial International Search for PCT Application No. PCT/US2007/006530, mailed Jul. 31, 2007, 7 pages.
International Search Report for PCT Application No. PCT/US2007/006530, mailed Nov. 12, 2007, 7 pages.
Written Opinion for PCT Application No. PCT/US2007/006530, mailed Nov. 12, 2007, 10 pages.
Invitation to Pay Additional Fees and Partial International Search for PCT Application No. PCT/US2009/030019, mailed Jun. 5, 2009, 5 pages.
International Search Report for PCT Application No. PCT/US2009/030019, mailed Jul. 20, 2009, 7 pages.
Written Opinion for PCT Application No. PCT/US2009/030019, mailed Jul. 20, 2009, 9 pages.
Invitation to Pay Additional Fees and Partial International Search for PCT Application No. PCT/US2008/087690, mailed May 15, 2009, 5 pages.
International Search Report for PCT Application No. PCT/US2008/087690, mailed Aug. 11, 2009, 7 pages.
Written Opinion for PCT Application No. PCT/US2008/087690, mailed Aug. 11, 2009, 10 pages.
Extended Search Report issued for European Patent Application No. 11153615.7, mailed on Dec. 15, 2011, 8 pages.
Examination Report in European Patent Application No. 11153618.1, mailed on Oct. 14, 2013, 5 pages.
Extended Search Report issued for European Patent Application No. 11153618.1, mailed on Dec. 12, 2011, 9 pages.
Extended Search Report issued for European Patent Application No. 13168508.3, mailed on Oct. 24, 2013, 7 pages.
Office Action mailed on Apr. 9, 2013 for Japanese Patent Application No. 2010-539873, English translation of "Notification of Reason for Rejection", 6 pages.
Examination Report in Mexican Patent Application No. MX/a/2008/011714, mailed on Jan. 19, 2012.
Examination Report in Mexican Patent Application No. MX/a/2010/012213, mailed on Jan. 16, 2014, 3 pages.
International Application Serial No. PCT/US2010/045897, International Search Report and Written Opinion, mailed Dec. 28, 2010, 12 pages.
International Application Serial No. PCT/US2010/047811, Invitation to Pay Additional Fees and Partial Search Report, mailed on Dec. 2, 2010, 8 pages.
International Application No. PCT/US2011/033329, International Search Report and Written Opinion, mailed Nov. 23, 2011, 16 pages.
International Application No. PCT/US2011/033329, Invitation to Pay Additional Fees and Partial Search Report, mailed Aug. 4, 2011, 5 pages.
International Application Serial No. PCT/US2011/044508, International Search Report and Written Opinion mailed Dec. 1, 2011, 11 pages.
International Application Serial No. PCT/US2013/061494, Invitation to Pay Additional Fees and Partial Search Report, mailed Jan. 28, 2014, 6 pages.
First Examiner Report received for Australian Application No. 2010284216 mailed Mar. 20, 2014, 5 pages.
Examiner Report received for Japanese Application No. 2011-508709 mailed Mar. 4, 2014, 5 pages (3 pages of English Translation and 2 pages of Office Action).
Examination Report received for Chinese Patent Application No. 201180030341.8 mailed Jul. 2, 2014, 7 pages of Official copy only.
Examination Report received for Chinese Patent Application No. 200980126549.2 mailed Apr. 28, 2014, 3 pages of Official copy only.
Examination Report received for Chinese Patent Application No. 201080046911.8 mailed May 6, 2014, 8 pages of Official copy only.
Examination Report received for Japanese Patent Application No. 2012-525667 mailed on Jun. 6, 2014, 9 pages (5 pages of English Translation and 4 pages of Official Copy).
Examination Report received for Mexican Patent Application No. MX/a/2010/012213 mailed Apr. 16, 2014.
Examination Report received for Mexican Patent Application No. MX/a/2013/013831 mailed on Mar. 26, 2014, 1 page of Official copy only.
International Application No. PCT/US2012/065874, International Preliminary Report on Patentability mailed May 30, 2014, 7 pages.
International Application No. PCT/US2012/065874, International Search Report and Written Opinion mailed Aug. 7, 2013, 13 pages.
International Application No. PCT/US2013/061443, International Search Report mailed on Jan. 21, 2014, 3 pages.
International Application No. PCT/US2013/061494, International Search Report and Written Opinion mailed May 28, 2014, 21 pages.
Examination Report Received for Chinese Patent Application No. 201080046911.8 mailed on Dec. 3, 2014, 6 pages.

(56) References Cited

OTHER PUBLICATIONS

Examination Report Received for Mexican Patent Application No. MX/a/2012/002063 mailed on Feb. 27, 2015.
Examination Report Received for Mexican Patent Application No. MX/a/2010/012213 mailed on Jan. 5, 2015.
PCT International Patent Application No. PCT/US2011/033329, International Preliminary Report on Patentability mailed Nov. 1, 2012, 13 pages.
PCT International Patent Application No. PCT/US2010/045897, International Preliminary Report on Patentability mailed Mar. 1, 2012, 9 pages.
PCT International Patent Application No. PCT/US2013/061443, International Preliminary Report on Patentability issued Mar. 24, 2015, 9 pages.
PCT International Patent Application No. PCT/US2013/061494, International Preliminary Report on Patentability issued Mar. 24, 2015, 13 pages.
Examination Report Received for European Patent Application No. 10760475.3, mailed on Apr. 7, 2015, 7 pages.
PCT International Patent Application No. PCT/US2014/057158, International Search Report and Written Opinion mailed Mar. 30, 2015, 14 pages.

\* cited by examiner

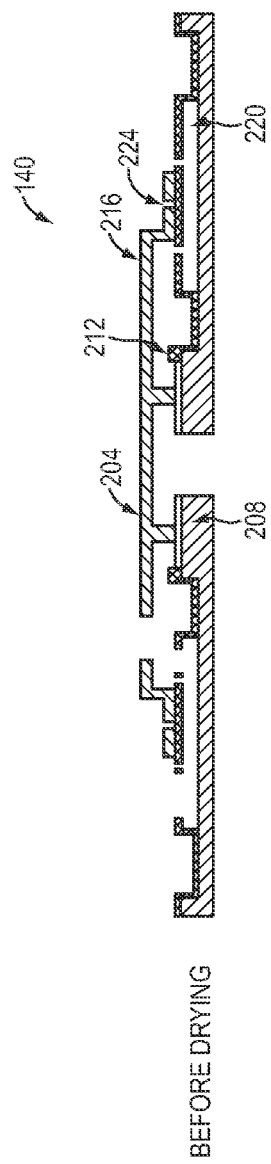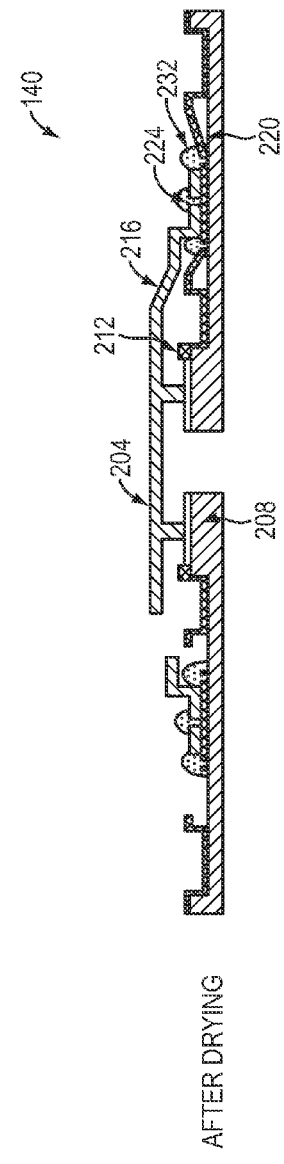

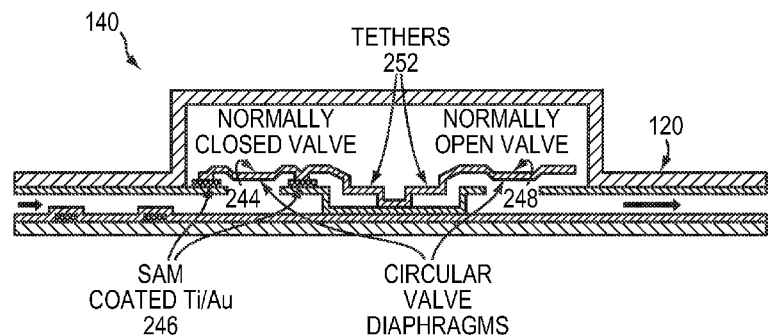
FIG. 19
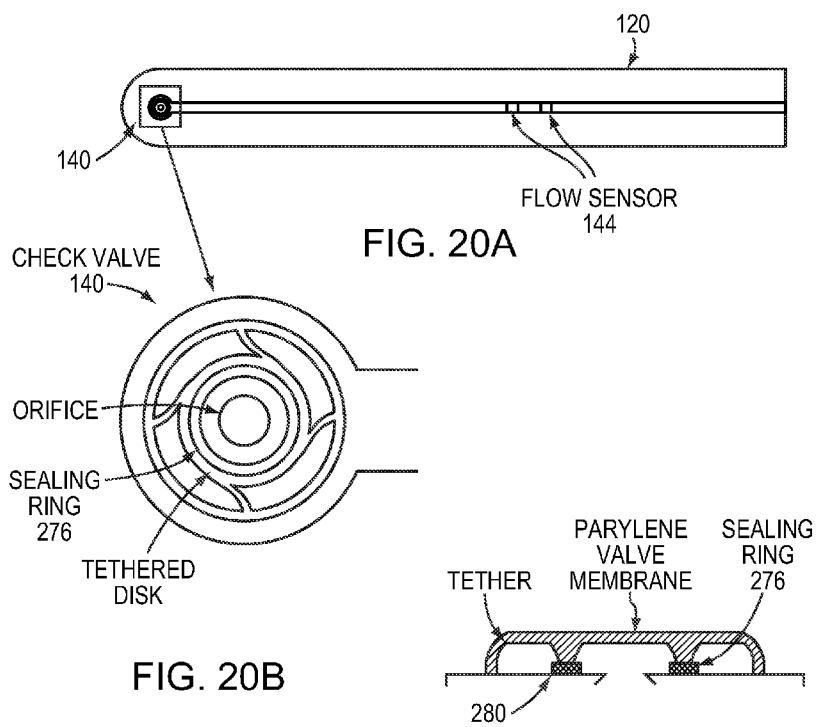
FIG. 20A
FIG. 20B
FIG. 20C

IMPLANTABLE PUMPS AND CANNULAS THEREFOR

CROSS-REFERENCE TO RELATED APPLICATIONS

This application claims priority to and the benefit of, and incorporates herein by reference in their entireties, U.S. Provisional Patent Application Nos. 61/051,422, which was filed on May 8, 2008; 61/197,751, which was filed on Oct. 30, 2008; 61/197,769, which was filed on Oct. 30, 2008; 61/198,090, which was filed on Nov. 3, 2008; and 61/198,131, which was filed on Nov. 3, 2008.

TECHNICAL FIELD

In various embodiments, the invention relates to implantable pumps and to cannulas for such pumps.

BACKGROUND

Medical treatment often requires the administration of a therapeutic agent (e.g., medicament, drugs, etc.) to a particular part of a patient's body. As patients live longer and are diagnosed with chronic and/or debilitating ailments, the likely result will be an increased need to place even more protein therapeutics, small-molecule drugs, and other medications into targeted areas throughout the patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted (and generally offer limited ability to change the dose in response to the clinical picture).

Another example is cancer, such as breast cancer or meningiomas, where large doses of highly toxic chemotherapies, such as rapamycin, bevacizumab (e.g., Avastin), or irinotecan (CPT-11), are typically administered to the patient intravenously, which may result in numerous undesired side effects outside the targeted area. Yet another example is drug delivery to the knee, where drugs often have difficulty penetrating the avascular cartilage tissue for diseases such as osteoarthritis.

Implantable drug-delivery devices, which may have a refillable drug reservoir, a cannula for delivering the drug, etc., generally allow for controlled delivery of pharmaceutical solutions to a specified target. The devices may be either passively controlled or actively controlled. In a passively-controlled device, drug is pumped out when, for example, a finger is pressed on the drug reservoir. In an actively-controlled device, drug may be pumped out automatically, for example at regular intervals or continuously over time. In either case, as drug within the drug reservoir depletes, the physician can refill the reservoir with, for example, a syringe, while leaving the device implanted within the patient's body. This approach can minimize the surgical incision needed for implantation and typically avoids future or repeated invasive surgery or procedures.

A variety of challenges, however, are associated with refillable drug-delivery devices. One limitation of conventional drug-delivery devices is that they are typically unable to dynamically respond to changes inside the device (e.g., failures, blockages, etc.) or to changes in the drug-delivery target. For example, tissue growth at the outlet of an implanted device (e.g., at the outlet of the cannula) may create a fluidic restriction. In this case, passive and active drug-delivery devices with no feedback control would likely not deliver the desired flow rate or dose of the drug. Similarly, without feedback, the desired flow rate or dose may not be delivered in the presence of temperature fluctuations, where there are variations in the drug-delivery device due to varying manufacturing processes, where different drug formulations are administered, etc.

A need exists, therefore, for improved implantable drug-delivery devices.

SUMMARY OF THE INVENTION

In various embodiments, the present invention features an implantable drug-delivery pump that is able to respond to changes that occur inside the pump and/or in the drug-delivery target. This ability of the pump improves its therapeutic value, and also enhances patient safety. For example, embodiments of the pumps described herein include one or more flow sensors for monitoring liquid (e.g., drug) flow through a cannula of the pump. Where, for example, the flow rate deviates from a desired rate, circuitry within the pump may take corrective action. Alternatively or in addition, the pumps described herein may include one or more pressure sensors for monitoring pressure in at least a portion of the pump. If necessary or desirable, circuitry within the pump may again adjust the pump operation based on the monitored pressure. In various embodiments, the flow sensor(s) is/are positioned within the cannula of the pump. The pressure sensor(s) may likewise be so placed, or be placed at other locations within the pump.

Various other components may also be present within, for example, the pump's cannula to further assure patient safety. For example, the cannula may include a filter to prevent the passage of large particles and possible air bubbles therethrough and to the patient, and/or a check valve to prevent backflow from a target site to a drug reservoir of the pump.

In general, in one aspect, embodiments of the invention feature an implantable pump that includes a drug reservoir, a cannula for conducting liquid from the reservoir, means for forcing liquid from the reservoir through the cannula, a sensor for monitoring a parameter (such as flow rate or pressure) relating to liquid flowing through the cannula, and circuitry for adjusting the forcing means based on the monitored parameter. The sensor may be manufactured, at least in part, from parylene, and may be electrically connected to the circuitry via metal lines running along the cannula.

The circuitry may be programmed to deliver a predetermined dosage of drug through the cannula, and the sensor may be a flow sensor. For example, the flow sensor may be a thermal flow sensor. A thermal flow sensor in accordance herewith may include a single element, physically associated with the cannula, that functions both as a heater and as a temperature sensor. Alternatively, the thermal flow sensor may include both a heater and an independent temperature sensor that are physically associated with the cannula. The temperature sensor may be located downstream of the heater. In still another alternative, the thermal flow sensor includes a heater and first and second temperature sensors, all of which are physically associated with the cannula. The first temperature sensor may be located downstream of the heater and the second temperature sensor may be located upstream of the heater.

In another embodiment, the flow sensor is a time-of-flight sensor. A time-of-flight sensor may include a heater and a first temperature sensor that are both physically associated with the cannula. The first temperature sensor may be located downstream of the heater, and the circuitry may cause (i) a discrete pulse of power to be applied to the heater and (ii) detection, by the first temperature sensor, of liquid heated by the heater. In some cases, a second temperature sensor is physically associated with the cannula and located upstream of the heater. Alternatively, one or more second temperature sensors may be physically associated with the cannula and located downstream of the heater.

In yet another embodiment, the time-of-flight sensor includes two upstream electrodes and two downstream electrodes that are all physically associated with the cannula. The circuitry may cause (i) a discrete voltage pulse to be applied across the two upstream electrodes and (ii) detection, by the two downstream electrodes, of an electrochemical pulse generated in the liquid flowing through the cannula.

In yet other embodiments, the flow sensor includes a pressure sensor in the reservoir and/or one or more pressure sensors in the cannula. Moreover, in addition to the flow sensor, the pump may further include a temperature sensor that is not in proximity to the flowing liquid and that facilitates compensation for fluctuations in an ambient temperature.

In various embodiments, the forcing means includes an electrolyte chamber, an expandable diaphragm that separates the chamber and the drug reservoir and that provides a fluid barrier therebetween, and electrolysis electrodes for causing evolution of a gas in the electrolyte chamber to thereby expand the diaphragm so that liquid is forced from the drug reservoir into the cannula.

Alternatively or in addition to a flow sensor, a pressure sensor may be included to monitor pressure within the cannula. In one embodiment, the pressure sensor is located at a distal end of the cannula (either inside or outside the cannula) for measuring pressure at the target site. The circuitry may then adjust pump operation based on the monitored pressure at the target site. In another embodiment, the pump includes a check valve in the cannula, and the pressure sensor is located inside the cannula and downstream of the check valve. In yet another embodiment, the pressure sensor is placed in the drug reservoir or in proximity to an interface between the cannula and the drug reservoir.

Embodiments including a pressure sensor may also include a flow sensor for monitoring a flow rate of the liquid through the cannula. The circuitry may then detect a pump malfunction based on the monitored pressure and/or the monitored flow.

In general, in yet another aspect, embodiments of the invention feature a cannula for an implantable pump. The cannula may include an elongate body that has a channel therethrough and that narrows at a distal end thereof, a filter integral with the body at a proximal end thereof, and means for connecting the proximal end of the body to a connection port of the implantable pump. The filter may have a cross-section larger than the flow cross-section of the channel, and may define openings that each have a height no greater than 2 µm. For example, the filter may include an array of parylene posts that define the openings.

In various embodiments, the cannula further includes a flow sensor for sensing fluidic flow within the channel, a pressure sensor for sensing pressure at a site into which the cannula is inserted, an electrochemical sensor coupled to a distal end of the elongate body and on an outside surface thereof, and/or a check valve for preventing a backflow of fluid in the channel. The elongate body of the cannula may be manufactured, at least in part, from parylene, and at least a portion of the body may be surrounded by a silicone structure.

In one embodiment, the cannula's check valve is normally closed and has a cracking pressure that is governed by a preloaded force applied to the check valve. The preloaded force may be caused by static friction ("stiction") and a difference in height between two components of the check valve. The check valve may be manufactured, at least in part, from layers of parylene. Moreover, a bonding agent may be applied to the check valve, and/or the check valve may include at least one micro heater, in order to maintain the preloaded force.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations, even if not made explicit herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 16 is a schematic sectional side view of a check valve prior to drying, in accordance with one embodiment of the invention;

FIG. 17 is a schematic sectional side view of the check valve of FIG. 16 after drying;

FIG. 19 is a schematic sectional view of a cannula that includes a band-pass check valve in accordance with one embodiment of the invention;

FIG. 20A is a schematic sectional plan view of a cannula that includes a check valve in accordance with another embodiment of the invention;

FIG. 20B is a schematic sectional plan view of the check valve of FIG. 20A;

FIG. 20C is a schematic sectional side view of the check valve of FIG. 20A;

DESCRIPTION

In general, embodiments of the present invention pertain to drug-delivery pumps implantable within a patient's body, such as, for example, within the patient's eye or brain. In certain embodiments, the implantable drug-delivery pumps combine small size and a refillable drug reservoir. The small size minimizes discomfort from the drug-delivery pump to the patient, while the refillable reservoir allows the pump to be refilled in situ, rather than having to be replaced. As such, a fluid, such as a solution of a drug, can be supplied to the patient over extended periods of time.

Figure 1A:
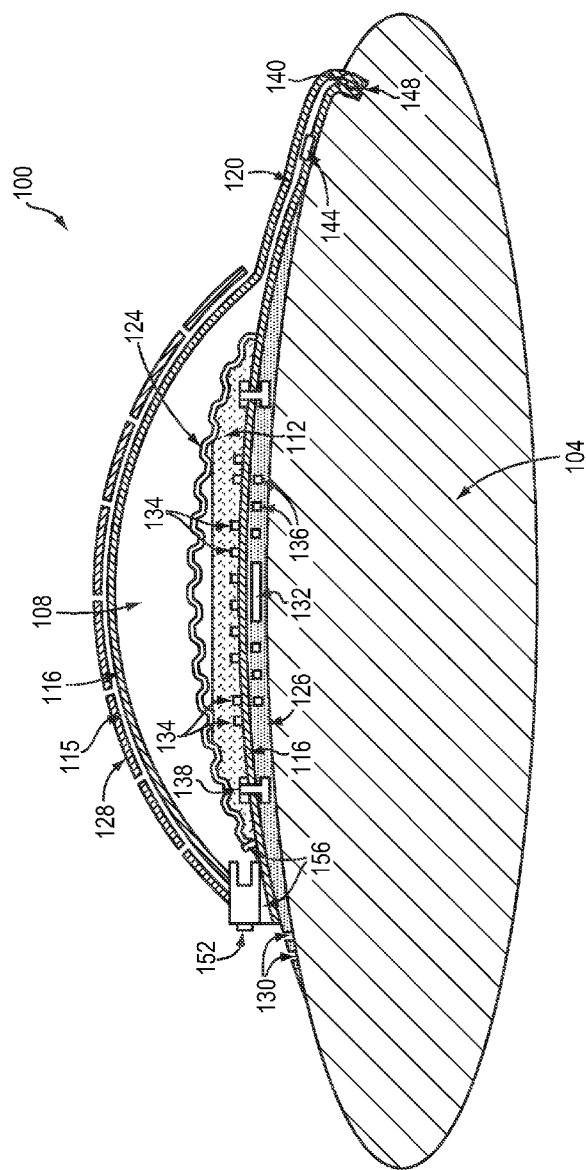
FIG. 1A schematically illustrates, in cross-section, an implantable drug-delivery pump in accordance with one embodiment of the invention.
Figure 1B:
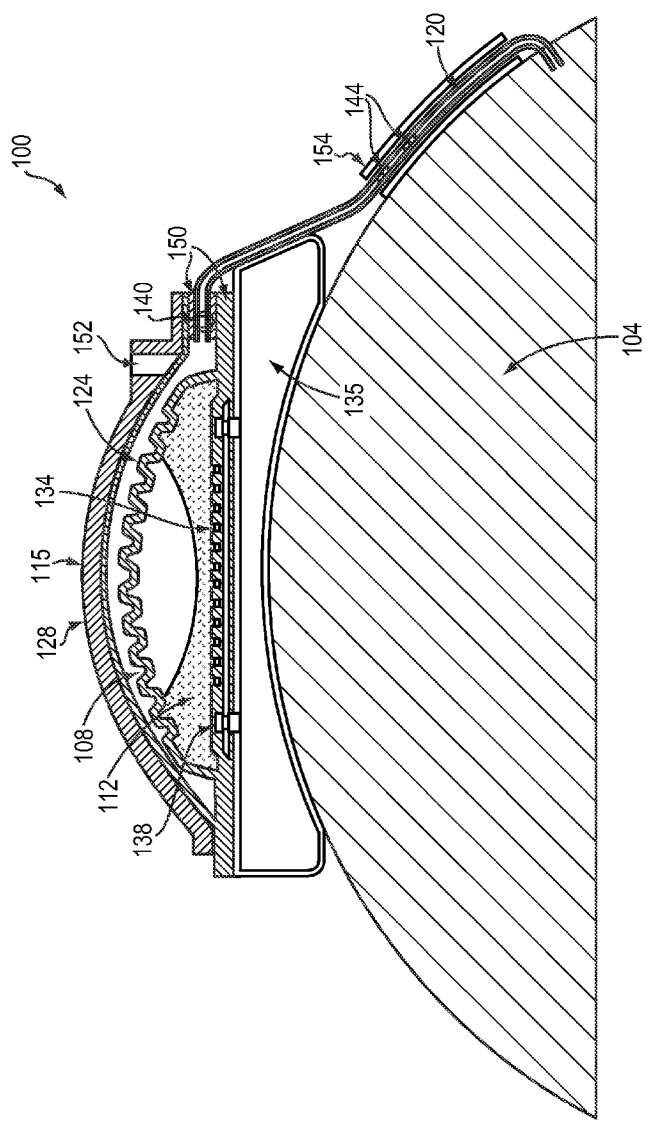
FIG. 1B schematically illustrates, in cross-section, an implantable drug-delivery device in accordance with another embodiment of the invention.

Embodiments of the invention may be employed in connection with various types of implantable drug-delivery pumps. FIGS. 1A and 1B schematically illustrate two variations of one such implantable drug-delivery pump 100 (namely, an exemplary electrolytic pump 100) implanted within a patient's eye 104. The pump 100 may instead, however, be implanted in other portions of a patient's body. For example, it may be implanted in the sub-arachnoid space of the brain to provide chemotherapy or to provide another type of treatment for the brain (e.g., by dosing the brain's parenchyma directly), or near a tumor in any portion of the patient's body to provide chemotherapy, or in a pancreas that does not respond well to glucose to provide agents (e.g., proteins, viral vectors, etc.) that will trigger insulin release, or in the knee to provide drugs that will treat osteoarthritis or other cartilage diseases, or near the spine to provide pain medications or anti-inflammatories, or elsewhere. As illustrated in FIGS. 1A and 1B, embodiments of the pump 100 may include two main components: a pair of chambers 108, 112 surrounded, at least in part, by a wall 115, and a cannula 120. As illustrated in FIG. 1A, the wall 115 that surrounds the chambers 108, 112 may include or consist of a stand-alone parylene film 116 and, thereover, a separate protection shell 128 made of a relatively rigid biocompatible material (e.g., medical-grade polypropylene). Alternatively, as illustrated in FIG. 1B, the wall 115 may correspond only to the protective shell 128, which may be coated with parylene. The top chamber 108 defines a drug reservoir that, when being used to treat a patient, may contain the drug to be administered in liquid form. For its part, the bottom chamber 112 may contain a liquid that, when subjected to electrolysis, evolves a gaseous product. For example, that liquid may be water, which may be electrolytically separated by an applied voltage into hydrogen gas and oxygen gas. Alternatively, as other examples, the electrolyte liquid may be a saline solution (i.e., NaCl and $H_2O$) or a solution that contains either magnesium sulfate or sodium sulfate. In one embodiment, the two chambers 108, 112 are separated by a corrugated diaphragm 124. In other words, the diaphragm 124 provides a fluid barrier between the two chambers 108, 112. Like the stand-alone film 116, the diaphragm 124 may be constructed from, for example, parylene.

As illustrated in FIG. 1A, the stand-alone film 116 may act as an outer barrier for the drug reservoir 108 and the protective shell 128 may provide a hard surface against which the film 116 exerts pressure. In such a case, the shell 128 may be perforated to allow for eye, brain, or other bodily fluid movement. Alternatively, as illustrated in FIG. 1B, the protective shell 128 may itself act as the outer barrier for the drug reservoir 108 and be unperforated. In both embodiments depicted in FIGS. 1A and 1B, the protective shell 128 may prevent outside pressure from being exerted on the drug reservoir 108. As illustrated in FIG. 1A, a bottom portion 126 (i.e., a floor 126) of the protective shell 128 may include suture holes 130. Similarly, although not shown in either FIG. 1A or FIG. 1B, the cannula 120 may also include suture holes along its sides. The suture holes 130 may be employed in suturing (i.e., anchoring) the pump 100 in place in the patient's body.

As also illustrated in FIG. 1A, to provide power to the pump 100 and to enable data transmission therewith, a battery and control circuitry 132 may be embedded (e.g., hermetically sealed) under the chambers 108, 112 (i.e., between a bottom portion of the stand-alone parylene film 116 of the drug reservoir 108 and the floor 126 of the protective shell 128), and an induction coil 136 may be integrated in the protective shell 128 (e.g., by injection molding). FIG. 1B more clearly illustrates a hermetic case 135 for housing the battery and conventional control circuitry 132, but, for simplicity, does not depict the components housed therein. The hermetic case 135 may be made from biocompatible metals (e.g., titanium) or metal alloys. The bottom of the hermetic case 135 may be flat, or it may be concave to help the implantable pump 100 fit on the patient's eye 104.

In one embodiment, the induction coil 136 permits wireless (e.g., radio-frequency) communication with an external device (e.g., a handset). The handset may be used to send wireless signals to the control circuitry 132 in order to program, reprogram, operate, calibrate, or otherwise configure the pump 100. In one embodiment, the control circuitry 132 communicates electrically with electrolysis electrodes 134 in the electrolyte chamber 112 by means of metal interconnects (vias) 138 spanning a bottom portion of the electrolyte reservoir 112. The electrolysis electrodes 134 may be made from, for example, platinum, gold, and/or other metal(s). As further described below, the control circuitry 132 also controls the pumping action of the pump 100, including the below-described closed-loop control process.

In one embodiment, as illustrated in FIG. 1A, the cannula 120 connects the drug chamber 108 to a check valve 140 inserted at the site of administration. Alternatively, or in addition, as illustrated in FIG. 1B, the check valve 140 may be integral with and located at a proximal end of the cannula 120 (i.e., at the end closest to the drug reservoir 108). More generally, however, the check valve 140 may be located anywhere along the cannula 120. In addition, one or more flow sensors 144 for monitoring the flow of the drug—and thereby enabling the measurement of drug volume—through the cannula 120 may be associated with one or more of a proximal, middle, or distal portion of the cannula 120. Optionally, as illustrated in FIG. 1A, a pressure sensor 148 may also be integrated at a distal end of the cannula 120 (i.e., at the end furthest from the drug reservoir 108) in order to measure pressure at the site of administration (e.g., the intravitreal chamber, shoulder capsule, knee capsule, cerebral ventricals, spinal canal, etc.). In one embodiment, the pressure sensor 148 provides feedback to the control circuitry 132 so that the flow of drug may be metered by a closed-loop control process. For example, increased pressure in the drug target region may cause a decrease in the flow of drug from the pump 100. Further pressure sensors 148 may be integrated along the cannula 120 or placed elsewhere in the pump 100, for example as described below with reference to FIG. 11. In addition, as further described below with reference to FIGS. 14 and 15, the cannula 120 may also include, for example at its proximal end, a filter to prevent the passage of large particles and possible air bubbles through the cannula 120 to the site of administration.

As illustrated in FIG. 1A, the cannula 120 may be an extension of the stand-alone parylene film 116. Alternatively, as illustrated in FIG. 1B, the cannula 120 may be a separate component (e.g., a parylene component) that is coupled to the protective shell 128. For example, a proximal end of the cannula 120 may be inserted through a fluid connection port formed in the protective shell 128 and be bonded thereto by way of, e.g., a biocompatible epoxy glue 150. A silicone sheath 154 may be placed around a portion of the cannula 120 (see FIG. 1B), but this is optional (see FIG. 1A).

In one embodiment, as illustrated in FIG. 1A, a fill port 152 is assembled with the drug reservoir 108 and sealed by a sealant (e.g., a biocompatible epoxy) 156 to the stand-alone film 116 and protective shell 128. In yet another embodiment, as illustrated in FIG. 1B, a hole may be formed through the protective shell 128 and the fill port 152 featured therein. In still another embodiment, the fill port 152 may be formed elsewhere on the pump 100 and be connected to the drug reservoir 108 through tubing. For example, the fill port 152 may be molded from biocompatible materials, coupled to a matching notch on the hermetic case 135, and connected to the drug reservoir 108 through the tubing. In one embodiment, the tubing is inserted through a fluid connection port formed in a wall surrounding the drug reservoir 108 and bonded thereto by way of a biocompatible epoxy glue. In either case, the fill port 152 is in fluid communication with the drug reservoir 108 and permits an operator of the pump 100 (e.g., a physician) to refill the drug reservoir 108 in situ (e.g., while the pump 100 is implanted within the patient's eye 104). In general, the drug reservoir 108 can be refilled by inserting a refill needle into and through the fill port 152.

In various embodiments, the main parts of the pump 100 (i.e., the pair of chambers 108, 112 and the cannula 120) are amenable to monolithic microfabrication and integration using multiple parylene layer processes. The fill port 152, the protective shell 128, and other components may be assembled with the pump 100 after the microfabrication steps.

In operation, when current is supplied to the electrolysis electrodes 134, the electrolyte evolves gas, expanding the corrugated diaphragm 124 (i.e., moving the diaphragm 124 upwards in FIGS. 1A and 1B) and forcing liquid (e.g., drug) to be conducted out of the drug reservoir 108, into and through the cannula 120, and out the distal end thereof to the targeted site of administration. The corrugations or other folds in the expandable diaphragm 124 permit a large degree of expansion, without sacrificing volume within the drug reservoir 108 when the diaphragm 124 is relaxed. When the current is stopped, the electrolyte gas condenses back into its liquid state, and the diaphragm 124 recovers its space-efficient corrugations.

A. Flow Sensors

As described herein, any of several flow sensors 144, including flow sensors based upon thermal effects, time-of-flight, and/or pressure, may be used in the implantable pump 100. In general, the flow sensor(s) 144 are located within the cannula 120, as depicted in FIGS. 1A and 1B, and are employed to sense the fluidic flow within the cannula 120.

Figure 2A:
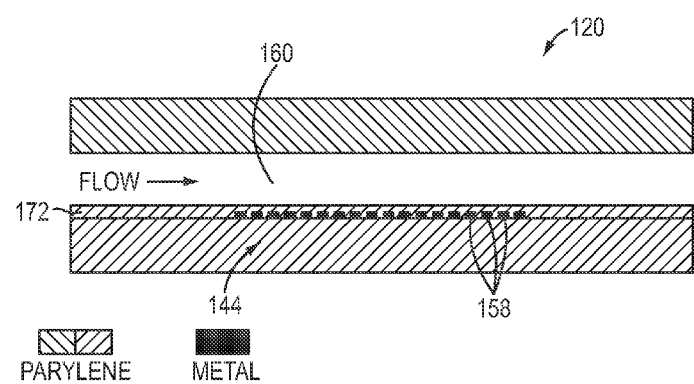
FIG. 2A schematically illustrates a generalized embodiment of a flow sensor that operates based upon thermal effects or time-of-flight.

In one embodiment, the flow sensors 144 are fabricated, at least in part, from parylene, which is a biocompatible, thin-film polymer. Advantageously, this enables the flow sensors 144 to be fully integrated into a parylene-based drug pump 100. With reference to FIG. 2A, which depicts a portion of a parylene-based cannula 120, the sensors 144 based upon thermal effects and time-of-flight may also include thin film metal elements 158 embedded in a parylene fluidic channel 160 of the cannula 120. As described further below, these thin film metal elements 158 can be used to create devices such as heaters and resistive temperature devices ("RTDs").

Figure 2B:
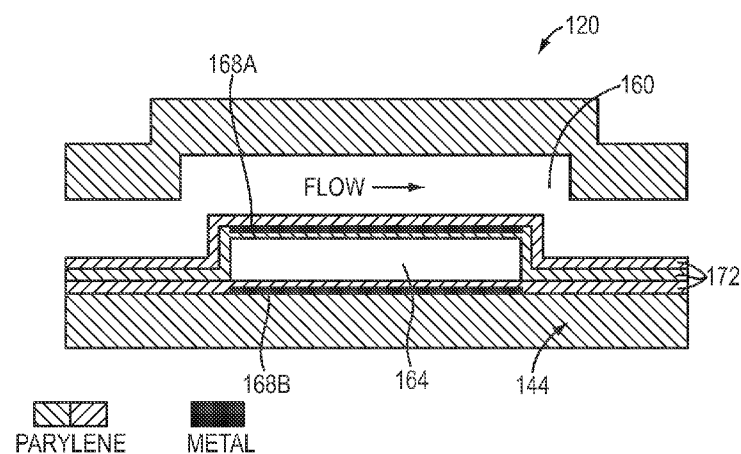
FIG. 2B schematically illustrates a capacitive pressure-sensing-based flow sensor in accordance with one embodiment of the invention.

Flow sensors 144 based upon pressure sensing can function in any of a variety of ways. For example, capacitive, piezoresistive, and piezoelectric techniques, among others known to those of ordinary skill in the art, may all be employed to advantage. An example of a parylene-based capacitive pressure sensor 144, positioned within the flow channel 160 of the cannula 120, is shown in FIG. 2B. Here, the flow sensor 144 includes an air chamber 164 enclosed between two capacitive plates or membranes 168A, 168B. The membranes 168A, 168B may be manufactured from, for example, a parylene/metal composite. The enclosed air chamber 164 may either be sealed or vented to atmospheric pressure. Then, increases in pressure above the sensor 144 (due to an increase in the rate of flow in the channel 160) cause the top membrane 168A to flex downward, which registers a capacitance change between the top and bottom membranes 168A, 168B. Similarly, decreases in pressure above the sensor 144 (due to a decrease in the rate of flow in the channel 160) cause the top membrane 168A to flex upward, which again registers a capacitance change between the top and bottom membranes 168A, 168B.

It may be desirable for parylene to be the only material in contact with bodily fluid or the drug flowing through the channel 160 of the cannula 120 (e.g., to ensure biocompatibility and also to protect the thin film metal elements 158 and metal electrodes 168A, 168B from degrading over time). Accordingly, as illustrated in FIGS. 2A and 2B, the sensors 144 may be encapsulated within one or more parylene layers 172. In addition, to strengthen the overall structure and to prevent mechanical damage, the sensors 144 may also be encapsulated within biocompatible silicone or epoxy.

In general, the flow sensors 144 interface to the control circuitry 132 (see FIG. 1A) of the pump 100. The control circuitry 132 is typically implemented on a printed circuit board ("PCB"), and metal traces from the flow sensors 144 to the control circuitry 132 may run parallel to the fluidic channel 160 of the cannula 120. At the actual interconnect with the circuitry 132, the parylene layer(s) 172 covering the metal may be etched away. The exposed metal pads may then be bonded to the PCB using conductive epoxy, solder, or another appropriate bonding agent.

A.1. Thermal Flow Sensors

In one embodiment, a thermal flow sensor 144 uses a resistive heater to locally heat the fluid flowing in proximity to the sensor 144. Then, as explained further below, the temperature of the flowing fluid, which can be measured using one or more miniature RTDs, provides an indication of the flow rate. One or more RTDs can either be adjacent to the heater, or in some cases the heater itself can be used simultaneously as the RTD.

A.1.a. Single-Heater Thermal Flow Sensor

Figure 3:
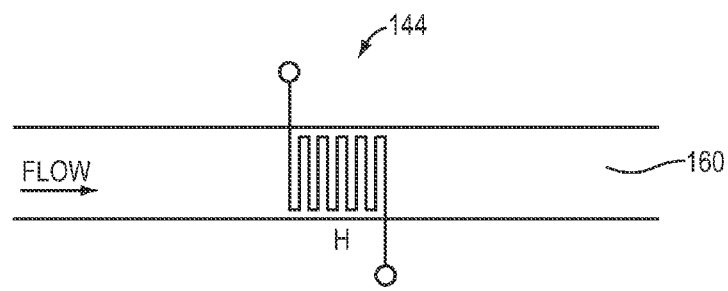
FIGS. 3-5 schematically illustrate thermal-effect flow sensors in accordance with various embodiments of the invention.

With reference to FIG. 3, in this configuration of the thermal flow sensor 144 there is only a single heater (denoted as "H" in FIG. 3 and in some of the figures that follow) physically associated with the cannula 120. Here, the heater is also used as a temperature sensor. The heater may be driven by the control circuitry 132 using either constant power or constant current. Then, the voltage drop across the heater indicates the flow rate. More specifically, the voltage drop across the heater decreases with increasing flow rates through the fluidic channel 160, as increasing flow lowers the effective resistance of the heating coil by more quickly conducting heat away. While not shown, another temperature sensor outside the fluid channel 160 (e.g., outside the cannula 120 and away from the flowing fluid) may be used by the control circuitry 132 to compensate for ambient temperature fluctuations.

A.1.b. Single-Heater, Single-Temperature-Sensor Thermal Flow Sensor

Figure 4:
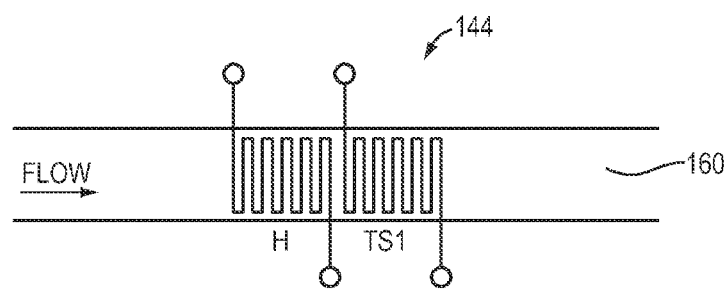

With reference to FIG. 4, in this configuration of the thermal flow sensor 144 there is one heater (H) and a single temperature sensor (denoted as "TS1" in FIG. 4 and in some of the figures that follow) positioned downstream of the heater. In this embodiment, the control circuitry 132 applies power to the upstream heater in order to heat fluid flowing past the heater, and the temperature sensed by the downstream temperature sensor increases with increasingly higher forward flow rates. More specifically, with increasingly higher forward flow rates for the fluid flowing in the channel 160, the heated fluid has less time to dissipate the heat before reaching the downstream temperature sensor. Again, while not shown, another temperature sensor outside the fluid channel 160 (e.g., outside the cannula 120 and away from the flowing fluid) may be used by the control circuitry 132 to compensate for ambient temperature fluctuations.

A.1.c Single-Heater, Dual-Temperature-Sensor Thermal Flow Sensor

Figure 5:
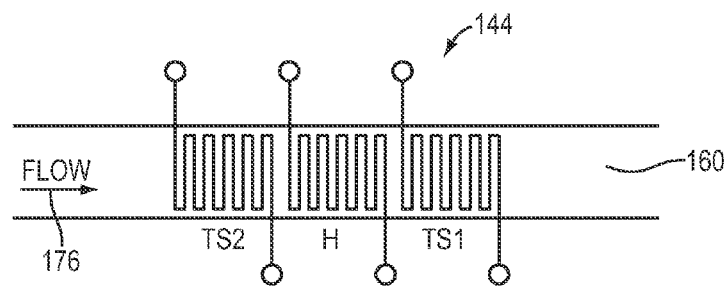

With reference to FIG. 5, in this configuration of the thermal flow sensor 144 there is a single heater (H), a first temperature sensor (TS1) positioned downstream of the heater, and a second temperature sensor (denoted as "TS2" in FIG. 5 and in some of the figures that follow) positioned upstream of the heater. Once again, the circuitry 132 applies power to the heater. The use of two temperature sensors allows for directional flow sensing. For example, with a forward flow (i.e., flow in the direction of the flow arrow 176 depicted in FIG. 5), the temperature measured by the downstream temperature sensor TS1 will increase while the temperature measured by the upstream temperature sensor TS2 will decrease. The opposite is true for a reverse flow (i.e., flow in the direction opposite to that of the flow arrow 176). In addition, while not shown, another temperature sensor outside the fluid channel 160 (e.g., outside the cannula 120 and away from the flowing fluid) may also be used by the control circuitry 132 to compensate for ambient temperature fluctuations.

Alternatively, using the configuration shown in FIG. 5, rather than measuring the temperatures of the two temperature sensors individually, the control circuitry 132 may instead measure a differential temperature between the two sensors in order to compute the flow rate. More specifically, if the first temperature sensor TS1 measures a higher temperature than the second temperature sensor TS2, fluid is flowing in the direction of the flow arrow 176. If the reverse is true, then fluid is flowing in a direction opposite to that of the flow arrow 176. For increasingly higher flow rates, the differential temperature measurement increases. A differential temperature measurement can give better sensitivity for measurements of the flow rate, as changes in the ambient temperature caused by means other than the heater will affect both temperature sensors in roughly the same manner and therefore be cancelled out.

The heater (H) in each of the embodiments depicted in FIGS. 3-5 may be operated continuously, or, alternatively, may be pulsed by the control circuitry 132. Pulsing the heater may lead to power savings since both the heater and the temperature sensors need not be active between flow measurements. For example, with reference to FIG. 5, the control circuitry 132 may apply a pulse of power to the heater for approximately 20 ms in order to bring it to a temperature of approximately 10° C. above ambient. Then, the differential temperature between the downstream and upstream temperature sensors TS1, TS2 may be averaged over approximately 60 ms, starting from the beginning of the heat pulse. This average differential temperature may then be directly correlated to the flow rate through the channel 160 of the cannula 120.

A.2. Time-of-Flight Flow Sensors

In one embodiment, a time-of-flight flow sensor 144 generates a tracer pulse in the fluid flowing within the channel 160 of the cannula 120, and then measures the time that it takes for this pulse to traverse a certain distance. This measured time is defined as the "time of flight" and corresponds to the linear fluid velocity, which may be translated into a volumetric flow rate. Some of the embodiments described below use a pulse of heated liquid as the tracer. In these embodiments, as before, the pulse of heated liquid can be detected using a miniature RTD. The magnitude of the time of flight depends upon the spacing of the heaters and temperature sensors, as well as the dimensions of the fluidic channel 160. In another embodiment described below, an electrochemical pulse is employed as the tracer. In this embodiment, a pair of electrodes may be used to detect the electrochemical pulse.

Figure 6:
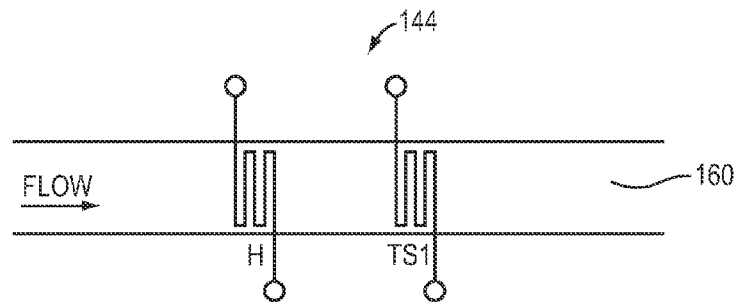
FIGS. 6-9 schematically illustrate time-of-flight-based flow sensors in accordance with various embodiment of the invention.

A.2.a. Single-Heater Time-of-Flight Flow Sensor with Single Downstream Temperature Sensor With reference to FIG. 6, in this configuration of the time-of-flight flow sensor 144 there is a single heater (H) and a single temperature sensor (TS1) positioned downstream of the heater. The control circuitry 132 may cause a discrete pulse of power to be applied to the upstream heater. The heater may then transfer a pulse of heat to the fluid flowing in the channel 160 of the cannula 120 in proximity to the heater. As this pulse of heated fluid travels downstream, it is detected by the downstream temperature sensor. The delay between the time of pulse generation and the downstream detection of the heated fluid is the time of flight. As the flow rate increases, the time of flight decreases.

Figure 7:
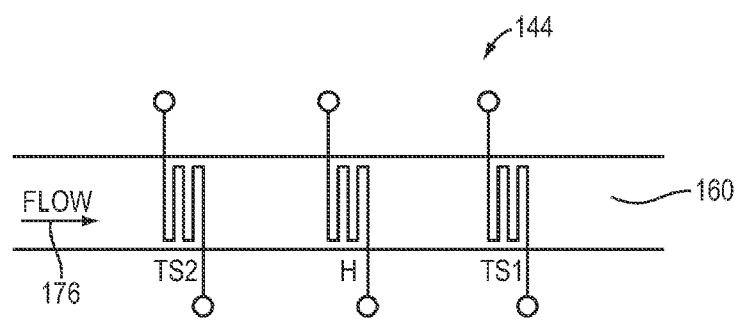

A.2.b. Single-Heater Time-of-Flight Flow Sensor with Downstream and Upstream Temperature Sensors With reference to FIG. 7, in this configuration of the time-of-flight flow sensor 144 there is a single heater (H), a first temperature sensor (TS1) positioned downstream of the heater, and a second temperature sensor (TS2) positioned upstream of the heater. Once again, the control circuitry 132 may cause a discrete pulse of power to be applied to the heater. The two temperature sensors may then be used to detect the heated pulse of fluid. More specifically, the use of the two temperature sensors allows for bi-directional flow sensing capability. For forward flows (i.e., flows in the direction of the flow arrow 176), the downstream temperature sensor will detect a thermal pulse while the upstream sensor will not. The opposite is true for reverse flows (i.e., flows in the direction opposite to that of the flow arrow 176).

In addition, besides measuring the signal at the two temperature sensors independently, the control circuit 132 may instead measure a differential signal between the two. This may yield a more precise detection of the flow direction, and the time-of-flight therefor, by eliminating temperature fluctuations not caused by the tracer pulse (e.g., ambient temperature fluctuations caused other than by the tracer pulse should affect each temperature sensor equally, and thereby be cancelled out).

Figure 8:
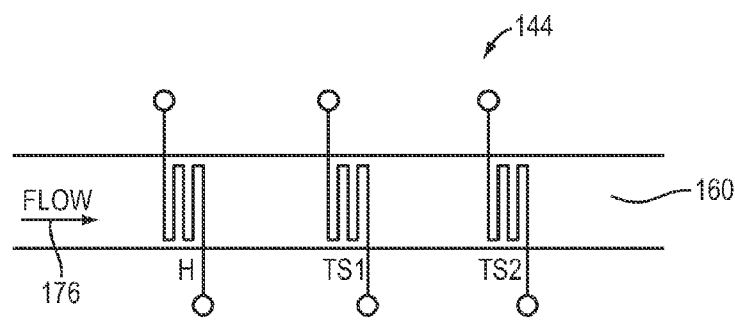

A.2.c. Single-Heater Time-of-Flight Flow Sensor with Multiple Downstream Temperature Sensors With reference to FIG. 8, in this configuration of the time-of-flight flow sensor 144 there is a single heater (H) and two (TS1, TS2) or more temperature sensors positioned downstream of the heater. Yet again, the control circuitry 132 may apply a discrete pulse of power to the heater. As the resulting thermal pulse of fluid travels downstream in the direction of flow arrow 176, it is initially detected by the first temperature sensor TS1 and then by the second TS2. Each of the delay times between the generation of the pulse of power and the detection of the resulting heated fluid pulse by the respective downstream temperature sensor can be used as an indication of the flow rate. In addition, a delay time between the thermal pulse passing the first temperature sensor and then passing the second temperature sensor can also be used to determine the flow rate. Also, the use of multiple downstream temperature sensors allows the flow sensor's range to be extended, as the temperature sensors closer to the heater are more suited for slower flow rates (as the heat pulse may dissipate from the fluid before reaching the further downstream sensors), while the temperature sensors further downstream are better suited for faster flow rates (as the heat pulse will likely still be present in the fluid when it reaches those further downstream sensors).

A.2.d. Time-of-Flight Flow Sensor Employing an Electrochemical Pulse

Figure 9:
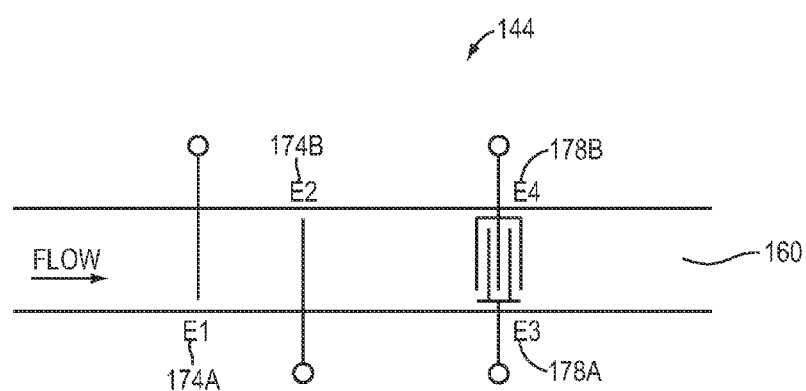

With reference to FIG. 9, in this configuration of the time-of-flight flow sensor 144 there is two upstream electrodes 174A, 174B and two downstream electrodes 178A, 178B. Each of the electrodes 174A, 174B, 178A, 178B may be in contact with the fluid flowing in the channel 160 of the cannula 120. In this embodiment, the control circuitry 132 may create an electrochemical pulse in the fluid using the two upstream electrodes 174A, 174B. More specifically, a discrete voltage pulse may be applied across the upstream electrodes 174A, 174B to electrochemically change the fluid in proximity to these electrodes 174A, 174B. Generally, these electrochemical changes are small changes in the ion concentration or pH of the fluid. The electrochemical pulse may then travel downstream with the fluid flow and be detected by the two downstream electrodes 178A, 178B. In particular, the control circuitry 132 may measure the impedance across the downstream electrodes 178A, 178B. In one embodiment, to prevent electrolysis, an AC impedance measurement is used. A change in impedance signals the presence of the electrochemical pulse. The delay between the time of pulse generation and the downstream detection of the electrochemical pulse is the time of flight. Again, as the flow rate increases, the time of flight decreases.

A.3. Pressure-Based Flow Sensors

Pressure-based flow sensors 144 may be employed at various locations of the implantable pump 100 to measure the pressure at key points in the fluidic system, and thereby deduce the fluid flow rate through the cannula 120. More specifically, the flow regimes encountered in, for example, ocular drug pumps 100 are usually laminar. As such, there is a well-understood, nearly linear (i.e., directly proportional) relationship between the measured pressure and the fluid flow rate.

A.3.a. Pressure-Based Flow Sensor in the Drug Reservoir

Figure 10A:
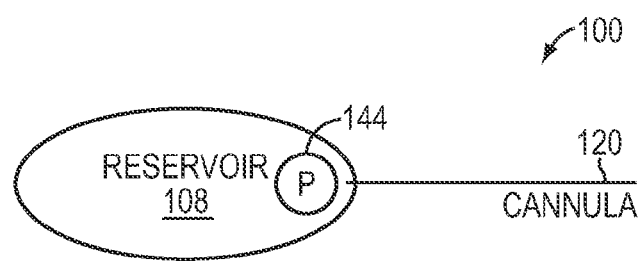
FIGS. 10A and 10B schematically illustrate pressure-sensing-based flow sensors in accordance with various embodiments of the invention.

With reference to FIG. 10A, in this configuration a single pressure-based flow sensor 144 is located inside the drug reservoir 108. For example, referring back to FIGS. 1A and 1B, the pressure sensor 144 may be integrated with the floor of the drug reservoir 108 just prior to the entry point of the cannula 120. Because the flow through the cannula 120 is laminar, the pressure measured in the drug reservoir 108 will be directly proportional to the fluid flow rate through the cannula 120, assuming that the pressure at the cannula 120 output does not change. More specifically, higher pressures measured inside the drug reservoir 108 are indicative of quicker fluid flow rates through the cannula 120, and lower pressures measured inside the drug reservoir 108 are indicative of slower fluid flow rates through the cannula 120.

A.3.b. Pressure-Based Flow Sensors in the Drug Reservoir and in the Cannula

Figure 10B:
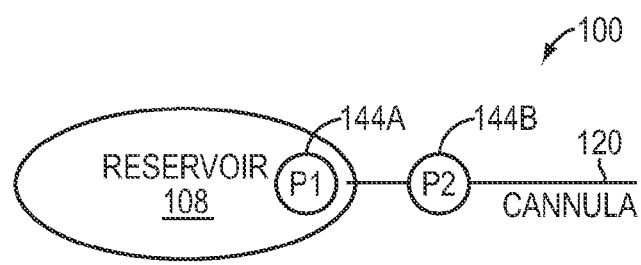

With reference to FIG. 10B, in this configuration a first pressure-based flow sensor 144A is located at the beginning (i.e., just outside the entry point) of the cannula 120, and a second pressure-based flow sensor 144B is located either at the end of the cannula 120 or within the length of the cannula 120. For example, as depicted in FIG. 10B, the first pressure sensor 144A is located inside the drug reservoir 108 just prior to the entry point of the cannula 120, and the second pressure sensor 144B is located approximately half-way up the length of the cannula 120. Again, because the flow through the cannula 120 is laminar, the difference in the pressures measured by the two pressure sensors 144A, 144B will be, as further described below with reference to FIG. 12, directly proportional to the fluid flow rate through the cannula 120. Advantageously, in this configuration, the relationship between the differential pressure measurement and the fluid flow rate through the cannula 120 is not affected by the pressure at the cannula 120 outlet.

A.4. Response to the Measured Flow Rates

In response to the measured flow rates, the control circuitry 132 may take corrective action in order to ensure that a correct dosage of drug be delivered through the channel 160 of the cannula 120 over time. For example, where the control circuitry 132 determines that a higher flow rate of drug is needed, it may increase the current to the electrolysis electrodes 134 to evolve greater gas in the electrolyte chamber 112, thereby further expanding the diaphragm 124 and increasing the fluid flow rate through the cannula 120. Alternatively, where the control circuitry 132 determines that a lower flow rate of drug is needed, it may decrease the current to the electrolysis electrodes 134 to evolve less gas in the electrolyte chamber 112, thereby lessening the expansion in the diaphragm 124 and decreasing the fluid flow rate through the cannula 120. Depending upon the particular application for which the pump 100 is employed, the flow rate requirements for fluid flowing through the cannula 120 may range from the nL/min to the μL/min flow scales.

B. Pressure Sensors

In another aspect, embodiments of the invention pertain to the placement of one or more pressure sensors 148 in the implantable drug pump 100 for the purposes of monitoring the drug target area and the health of the pump 100. For example, with reference to FIG. 11, one or more pressure sensors 148 can be placed in the drug reservoir 108, inside the cannula 120, or in both areas simultaneously for monitoring purposes. In each case, the control circuitry 132 within the pump 100 can receive (e.g., via metal traces connecting each pressure sensor 148 with the control circuitry 132) and process the pressure data. In addition, based on the pressure data, the control circuitry 132 can adjust operation of the pump 100 to avoid excess pressure, maintain an optimal pressure or pressure range, prevent harm to the patient in case of pump 100 failure, and/or compensate for environmental changes or changes in the drug regimen or the anatomical target. As further illustrated in FIG. 11, the cannula 120 of the pump 100 may also contain one or more of the check valves 140 and flow sensors 144 described herein.

B.1. Target Site Monitoring

A pressure sensor 148 located in or on the cannula 120 can be used to measure and monitor the local pressure at the injection site. For example, if knowledge of the injection-site pressure is required during infusion, then the pressure sensor 148 can be placed in either of two places: (i) inside the cannula 120 and at its distal tip (as illustrated by the placement of pressure sensor 148C in FIG. 11), or (ii) outside the cannula 120 and at its distal tip (as illustrated by the placement of pressure sensor 148B in FIG. 11). Advantageously, placement of a pressure sensor 148B, 148C at the distal tip of the cannula 120 prevents flow-related pressure drops inside the cannula 120 from causing an error in the pressure reading.

Figure 11:
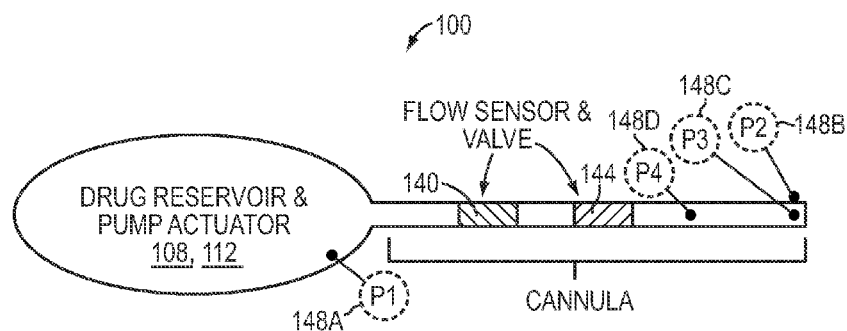
FIG. 11 schematically illustrates the placement of various pressure sensors in an implantable drug-delivery pump in accordance with one embodiment of the invention.

On the other hand, if knowledge of the injection site pressure is only needed when the implantable pump 100 is in the off state, then the sensor 148 can be placed (i) inside the cannula 120 and downstream of the check valve 140 (as illustrated by the placement of pressure sensors 148C and 148D in FIG. 11), or (ii) outside the cannula 120 and at its distal tip (as illustrated by the placement of pressure sensor 148B in FIG. 11). Placement of a pressure sensor 148 before the check valve 140 (as illustrated by the placement of the pressure sensor 148A in FIG. 11) can provide a measurement of the pressure in the drug reservoir 108.

As noted above, the pressure-sensor readings may be used by the control circuitry 132 to trigger responses by the pump 100. For example, for an ocular drug-delivery pump 100 containing glaucoma medication, the pump 100 may be activated, if the intraocular pressure (IOP) exceeds a certain value, to deliver a calculated dose of IOP-reducing drug. Pressure measurements may be time-averaged by the circuitry 132 to eliminate the possibility of false alarms (e.g., external pressure applied to the eye, sneezing, knee flexion, etc.). The subsequent lowering of the IOP may also be monitored by the pressure sensor 148. Such a configuration is especially suitable for acute cases, where the drug is delivered immediately upon IOP spikes. In chronic cases, where the pressure is monitored over the course of several days, the dosing schedule and volume of the drug delivered by the pump 100 may be varied, for optimal therapeutic value, based on the pressure data.

B.2. Pump Health Monitoring

Pressure sensors 148 located within the drug reservoir 108 and/or inside the cannula 120 may also be used by the control circuitry 132 to monitor the health of the pump 100 (e.g., to detect a pump 100 malfunction). The control circuitry 132 may do so by considering only data from the pressure sensors 148, or, alternatively, by analyzing pressure data from the pressure sensors 148 in conjunction with readings from one or more of the earlier-described flow sensors 144.

Together, the pressure and flow sensors 148, 144 form a multi-point failure-detection system. More specifically, with reference to FIG. 12, under normal operating conditions, the pressure drop across the cannula 120 ($\Delta P = P1-P2$ or $P1-P3$ or $P1-P4$, in FIG. 11) will follow a known relationship with the flow rate (Q) through the cannula 120, as measured by the flow sensor 140. This relationship can be expressed as the function $Q_{normal}(\Delta P)$. It should also be noted that in a situation where the magnitude of the pressure at the pump 100 outlet is significantly smaller than the pressure inside the pump 100, only a single pressure sensor 148A inside the drug reservoir 108 is needed. In this case, $\Delta P \approx P1$ (see FIG. 11).

Figure 12:
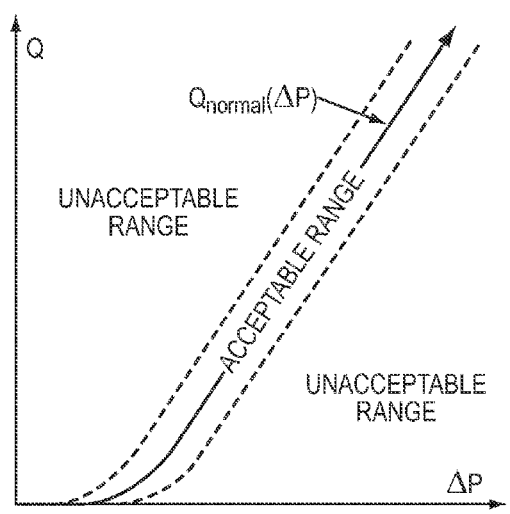
FIG. 12 is a graph illustrating the relationship, under normal operating conditions, between the pressure drop across a cannula for a typical implantable drug-delivery pump and the rate of fluid flow therethrough.

Any deviation from the expected relationship ($Q_{normal}(\Delta P)$) generally signals a problem with one or more of the pump's components. It is possible to define an acceptable range of pump states during which the pump 100 continues to operate normally. For example, FIG. 12 illustrates what constitutes an acceptable pump state. Unacceptable pump states, on the other hand (i.e., states outside the acceptable range to each side of the $Q_{normal}(\Delta P)$ line), should trigger action in the pump 100. These actions, which may be implemented by the pump's control circuitry 132, may include providing notification to the patient and/or doctor of a pump malfunction and/or putting the pump 100 in a standby mode. The notification may take place through a wireless transmission, as described above, to a handheld device, by audible sound, or by an optical signaling system built into the pump 100.

Besides comparing the pump state to a known function ($Q_{normal}(\Delta P)$), another approach is for the control circuitry 132 to compare the time-varying pump state during a dose that is in progress to the pump state(s) recorded by the control circuitry 132 for previous dosage(s). In such a case, any significant deviation indicates that something is out of the ordinary with the pump 100 and provides grounds for putting the pump 100 in the standby mode and/or notifying the patient/doctor.

For exemplary purposes, several possible failure scenarios and their detection are now described.

B.2.a. Leak in the Cannula

If a leak in the cannula 120 exists, the flow rate measured by the flow sensor 144 will be lower than expected given the measured pressure differential.

B.2.b. Blockage of the Cannula

If there is a blockage inside or at the outlet of the cannula 120, the flow rate measured by the flow sensor 144 will be lower than expected given the measured pressure differential.

B.2.c. Failure of the Check Valve

If the check valve 140 becomes stuck in the closed position, the flow sensor 144 will not register any flow even at pressures exceeding the check valve's cracking pressure. Conversely, if the check valve 140 becomes stuck in the open position, the flow sensor 144 will register a flow rate even at extremely low pressures.

B.2.d. Failure of the Pump's Actuator

If the pump 100 is being actuated (e.g., by operation of the electrolysis electrodes 134 in the electrolyte chamber 112), but there is no increase in the pressure in the drug reservoir 108 and no registered flow, then a problem with the pump's actuator is indicated. Similarly, if the pump 100 is being driven at a high rate and there is a lower-than-expected increase in differential pressure ($\Delta P$) and/or flow rate, this also signals a potential problem with the pump's actuator.

Of course, even with multiple pressure and/or flow sensors 148, 144, it may still be difficult to distinguish between all possible failure mechanisms. This may, however, be unimportant from a practical perspective, since often it is the existence of a problem—which may be inferred from any pump state outside the accepted range—that is of greater importance than its precise nature.

C. Filters, Check Valves, and Electrochemical Sensors for the Cannula

As described herein, the cannula 120 may be a multi-functional component of the drug-delivery pump 100. It may, as already described, include integrated flow sensors 144 and/or pressure sensors 148. Additional integrated functional components that the cannula 120 may feature include a filter to prevent the passage of large particles and possible air bubbles through the cannula 120 into the site of administration (e.g., a patient's eye 104), a check valve 140 to prevent a backflow of fluid from the target site into the cannula's channel 160, and an electrochemical sensor 312 (see FIG. 23) outside the cannula 120 at a distal end thereof.

Figure 13:
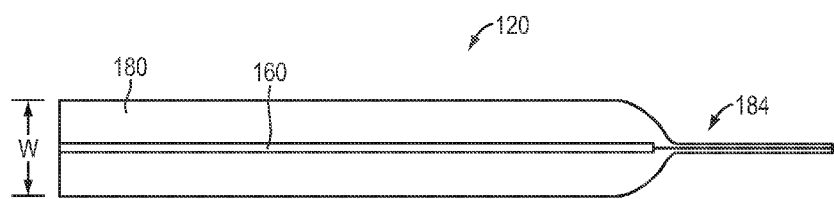
FIG. 13 is a schematic sectional view of a cannula in accordance with one embodiment of the invention.

FIG. 13 depicts a schematic sectional view of a cannula 120 in accordance with one embodiment of the invention. As illustrated, in this embodiment, the cannula 120 includes an elongate body 180 defining a channel 160 therethrough. Each of the body 180 and the channel 160 narrow towards a distal end 184 thereof. The small-diameter insertion tip of the cannula 120 aids in reducing surgical damage to the target region (e.g., the patient's eye 104). As previously mentioned, the elongate body 180 of the cannula 120 may include or consist essentially of parylene. Moreover, as described with reference to FIG. 1B (but not shown in FIG. 13, for simplicity), silicone (e.g., a silicone sheath 154, a silicone coating, etc.) may surround at least a portion of the cannula's parylene body 180 in order to provide a protective layer.

In one embodiment, the inner width of the channel 160 is approximately 100 µm, and the total width w of the elongate body 180 is approximately 400 µm. In this way, the channel width is large enough to facilitate the integration of one or more flow sensors 140, pressure sensors 148, and/or check valves 140. The edges of the body 180 may be used for routing electrical connections from each flow, pressure, and/or electrochemical sensor 144, 148, 312 to the control circuitry 132, as previously described (e.g., using conductive traces deposited on the edges of the body 180 and sealed, for example, by two parylene layers). In one embodiment, at the distal portion 184 of the cannula 120, the inner width of the channel 160 shrinks down to approximately 20 µm-50 µm, while the width of the elongate body 180 shrinks down to around approximately 100 µm.

C.1. Filter for the Cannula

Figure 14:
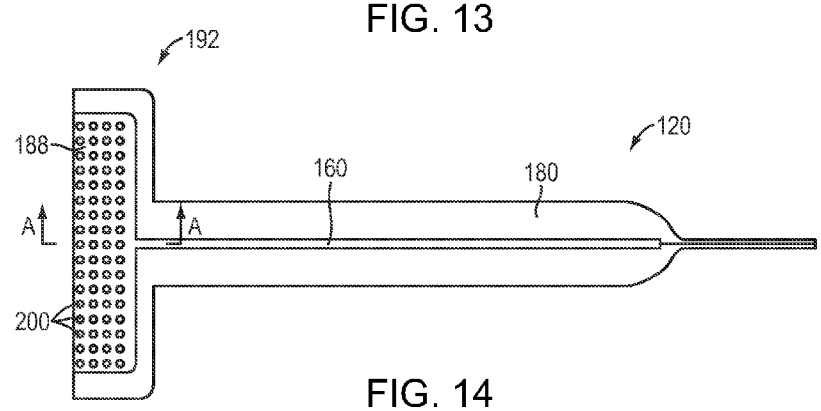
FIG. 14 is a schematic sectional view of a cannula, having a filter integrated at one of its ends, in accordance with one embodiment of the invention.

Small gas bubbles may be introduced into the drug reservoir 108 during the filling or refilling of the implantable drug-delivery pump 100 through the fill port 152, or may be generated by drug degassing. Although the small gas bubbles are generally harmless if they are injected into, for example, the patient's eye 104, they may affect the functions of the check valve 140, flow sensor(s) 144, and/or pressure sensor(s) 148 present in the channel 160 of the cannula 120. Accordingly, preventing gas bubbles from entering the channel 160 is highly desirable. As illustrated in FIG. 14, a filter 188 may be integrated with the proximal end 192 of the cannula's elongate body 180 for this purpose. More specifically, the filter 188, which may be a parylene mesh, may be bonded to the proximal end 192 of the cannula's elongate body 180 using, for example, a biocompatible epoxy glue. Alternatively, the filter 188 may be fabricated and integrated with the cannula 120 using the same parylene layers as are used to form the cannula's channel 160.

Figure 15:
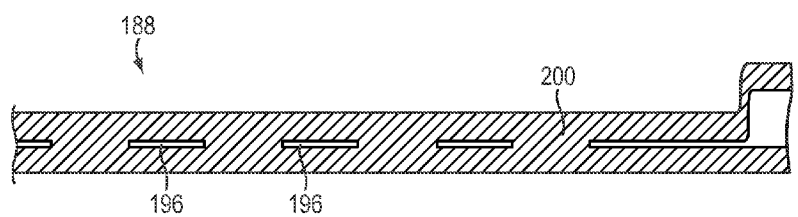
FIG. 15 is a schematic cross-sectional view of the filter depicted in FIG. 14, along the line A-A.

As illustrated in FIG. 14, the filter 188 may have a cross-section larger than a flow cross-section of the channel 160 so as to reduce the flow resistance in the filter 188. In one embodiment, as illustrated in FIG. 15, the filter 188 defines openings (e.g., channels) 196 that each have a cross-sectional dimension (e.g., a height) no greater than 2 µm (e.g., the openings 196 may be 1 µm to 2 µm high in cross-section) so as to prevent the passage of larger particles and gas bubbles into the channel 160 of the cannula 120. The openings 196 may be defined, as illustrated in FIGS. 14 and 15, by an array of parylene posts 200 in the filter 188. Moreover, the array of parylene posts 200 may prevent the clasping of top and bottom parylene layers of the filter 188.

C.2. Check Valve for the Cannula

In one embodiment, a preloaded force provides a preset cracking pressure (e.g., larger than 4 psi) for the check valve 140 of the cannula 120. In addition, the preloaded force aids in providing an effective seal in the check valve 140, thereby preventing a backflow of fluid through the cannula 120.

Figure 18:
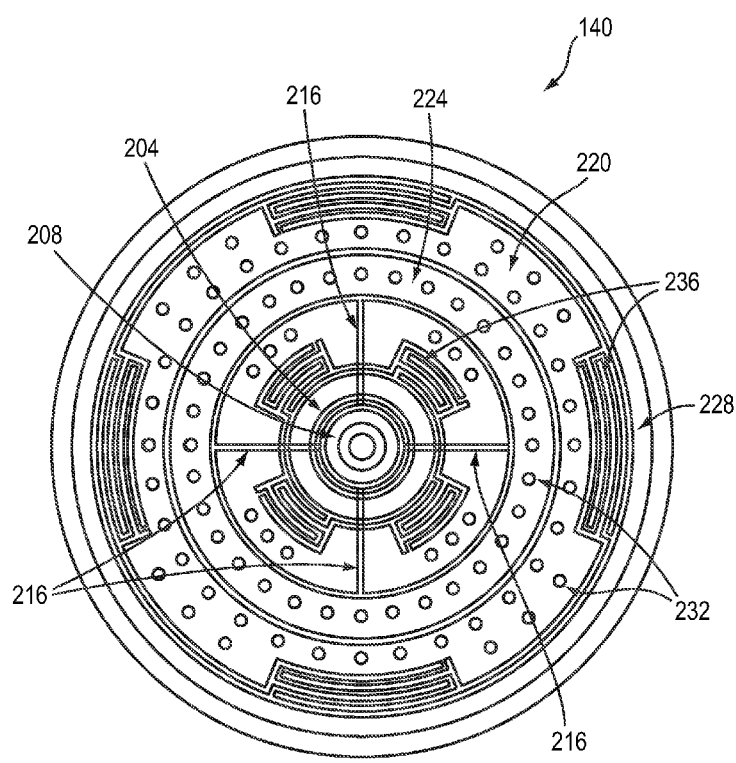
FIG. 18 is a schematic plan view of the check valve of FIG. 17.

A check valve 140 having a preloaded force applied thereto is shown in FIGS. 16-18 at various stages of manufacture. More specifically, FIG. 16 depicts the check valve 140 prior to it being dried (e.g., in air), while FIGS. 17 and 18 depict the check valve 140 after it has dried. In one embodiment, the check valve 140 is constructed from three parylene layers (e.g., a first layer for a sealing disk 204, a second layer for a valve seat 208, and a third layer for a stiction diaphragm 220), although in alternative embodiments other materials may also be used instead of, or in addition to, parylene. Preferably (although not necessarily), the material(s) used for the three layers is/are flexible, water-resistant, and biocompatible.

As illustrated in FIGS. 16-18, the main structure of the check valve 140 includes a circular sealing disk 204 positioned on top of a check valve seat 208. The check valve seat 208 may be constructed from, for example, a 20 µm thick parylene layer, and an initial step 212 (e.g., of 10 µm in thickness) may be created in the seat layer 208. In one embodiment, tethers 216 surround the sealing disk 204 and are anchored 224 to the center of the stiction diaphragm 220 in order to hold the sealing disk 204 in place. The tethers 216 may be constructed from, for example, parylene, and each tether 216 may have a thickness of approximately 5 µm. For its part, the stiction diaphragm 220 is anchored 228 to the lower level of the valve seat layer 208. The check valve 140 may be created by lithography (e.g., using sacrificial photoresist layers) or by any other appropriate means.

Because parylene adheres poorly to metal, a metal layer (e.g., Pt/Au 500 Å/2500 Å, or other metals with different thicknesses) may be deposited and employed to reduce the initial adhesion between the sealing disk 204 and the check valve seat 208. In this way, the pressure required to initially open the check valve 140 is reduced.

In one embodiment, after releasing all photoresist sacrificial layers in solvent as the last fabrication step, the stiction diaphragm 220 is left floating at its original position, which is at the same level as the check valve sealing seat 208, as shown in FIG. 16. However, after drying the check valve 140 (e.g., in air), stiction (due in part to the anchors 228 and soft tethers 236 of the stiction diaphragm 220) occurs between the lower level of the check valve seat 208 layer and the stiction diaphragm 220. A downward force towards the valve seat 208 (e.g., a preloaded force) is therefore created on the sealing disk 204 via the tethers 216, as shown by the bend in the tethers 216 in FIG. 17. After setting this preloaded force, a bonding agent 232 (e.g., epoxy) may be applied to permanently hold the stiction position and to prevent delamination between the tether anchors 224 and the stiction diaphragm 220. Multiple through holes may be formed in the sealing disk anchor 224 and stiction diaphragm 200 prior to application of the boding agent 232 in order that the bonding agent 232 reach all three parylene layers.

In one embodiment, micro metal resistor heaters are embedded between the three parylene layers. After stiction occurs and the force is loaded on the check valve sealing contact, current may be applied to the micro heaters in order to melt the three parylene layers and glue them together permanently.

In operation, the check valve 140 provides a unidirectional valve for the cannula 120 that allows a drug, or other fluid, to flow through the cannula 120 from the drug reservoir 108 to the treatment site, while preventing fluid from the treatment site from flowing through the cannula 120 and into the drug reservoir 108. More particularly, the flexible sealing disk 204 is tethered such that it my abut against, or flexibly extend from, the valve seat 208 depending upon the differential pressure above and below the sealing disk 204. For example, fluid flowing through the valve seat 208 towards the sealing disk 204 will force the sealing disk 204 to flexibly extend from the valve seat 208 (when the cracking pressure is exceeded), thereby allowing the fluid to pass through the check valve 140. In contrast, fluid flowing in the opposite direction creates a differential pressure that forces the sealing disk 204 to sealingly abut against the valve seat 208, thereby preventing fluid from flowing through the check valve 140. As a result, the check valve 140 provides a simple and efficient one-way valve system for the cannula 120.

FIG. 19 depicts an alternative embodiment of the check valve 140, namely a check valve 140 having a band-pass structure. The check valve 140 features two diaphragm valve portions 244, 248 tethered at a tethering location 252. The check valve 140 may be used, for example, to control fluid flow through the cannula 120 (e.g., by allowing fluid to flow in a forward direction only when a set pumping pressure is applied to the fluid, and/or preventing back-flow of fluid in a rearward direction).

In operation, the check valve's 140 cracking pressure prevents leakage through sealing portions 246 when the pump 100 is at rest, but the valve 140 will open to allow forward flow when a pumping action generates a pressure exceeding the cracking pressure. When the fluid experiences an extremely high (i.e., abnormal) pressure (e.g., due to an unexpected force during operation or implantation, etc.), the check valve 140 will shut down the forward the flow. In addition, the check valve 140 will prevent backward flow resulting from the intraocular pressure.

In greater detail, the check valve 140 includes a first, normally closed, valve 244 and a second, normally opened, valve 248. If a forward pressure below the cracking pressure of the first valve 244 is applied to the fluid in the cannula 120, the first valve 244 will remain closed and no fluid will flow. If, however, a forward pressure above the cracking pressure of the first valve 244 is applied to the fluid in the cannula 120, the first valve 244 will open, and the fluid will flow through both the first and second valves 244, 248. In addition, if the forward pressure exceeds a cracking pressure of the second valve 248, the second valve 248 will close, thereby preventing fluid flow therethrough. Finally, if a rearward pressure is applied to the fluid in the cannula 120, the first valve 244 will close, thereby preventing back-flow along the cannula 120.

With reference now to FIGS. 20A-20C, an embodiment of a single, normally closed, check valve 140, for example having a cracking pressure greater than 2 psi, is integrated into a cannula 120 upstream of a flow sensor 144. As before, the check valve 140 of this embodiment opens only when the pressure applied to a fluid in the cannula 120 is larger than the cracking pressure. With reference to FIGS. 20B and 20C, a parylene layer for a check valve sealing ring 276 of the check valve 140 may be directly deposited on a gold layer of a valve seat 280 (with, for example, an additional self-assembled monolayer coating on the gold surface). Due to the weak adhesion between gold and the parylene, this bond is easily released, thereby allowing the check valve 140 to open when the cracking pressure is exceeded. As there is no initial gap between the sealing ring 276 and the valve seat 280, no backward flow leakage is allowed.

Figure 21:
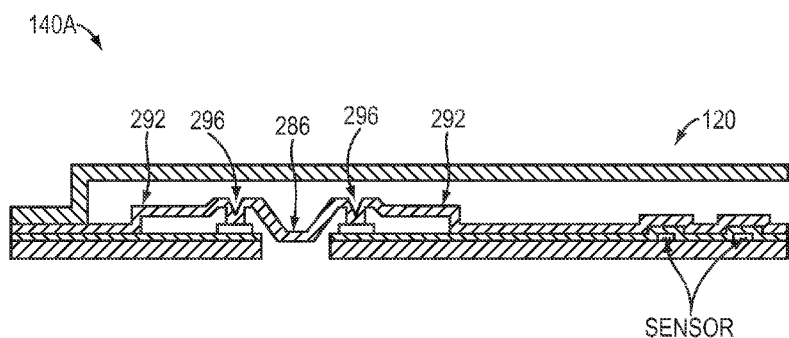
FIG. 21 is a schematic sectional view of a cannula that includes a check valve in accordance with yet another embodiment of the invention.
Figure 22:
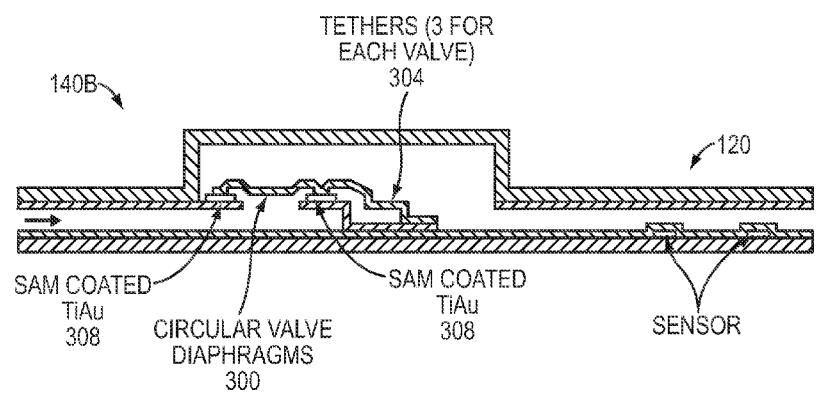
FIG. 22 is a schematic sectional side view a cannula that includes a check valve in accordance with still another embodiment of the invention.

Alternative embodiments of check valves 140A, 140B are shown in FIGS. 21 and 22, respectively. The check valves 140A, 140B include diaphragm valve portions 286, 300, tethers 292, 304, and sealing portions 296, 308 that are released upon a cracking pressure being exceeded. The cracking pressure (i.e., the minimum forward pressure to open each valve 286, 300) may be around 200 mmHg or 4 psi. Alternatively, higher or lower cracking pressures may be used.

C.3. Electrochemical Sensor for the Cannula

Figure 23:
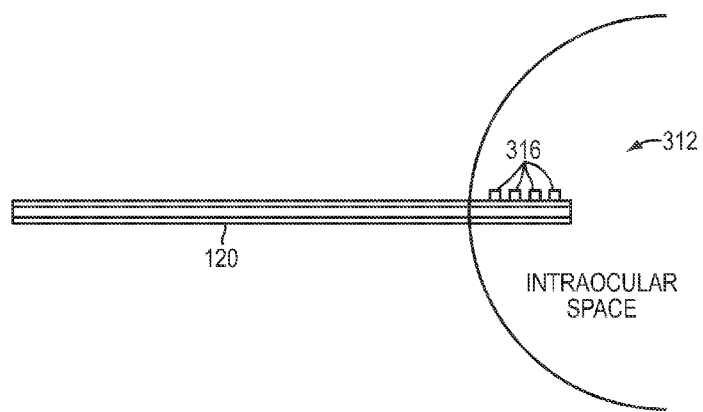
FIG. 23 schematically illustrates an electrochemical sensor coupled to a distal end of a cannula in accordance with one embodiment of the invention.

In one embodiment, as illustrated in FIG. 23, an electrochemical sensor 312 is placed on the cannula 120 (e.g., outside the cannula 120 on its distal tip) to provide in vivo monitoring of, for example, the drug concentration at the target site, such as the intraocular space, the cerebral spinal fluid, or the spine. As illustrated in FIG. 23, the sensor 312 may be placed on the cannula 120 so that it is completely immersed in the intraocular fluid after implantation of the cannula 120 in the patient's eye 104. The sensor 312 may, for example, operate based upon well known electrochemical detection principles such as linear voltammetry, cyclic voltammetry, pulsed voltammetry, and other techniques. These techniques generally involve the application of varying voltage waveforms to active electrodes 316 of the sensor 312. The oxidation and reduction of molecules on the electrode 316 surfaces generate current, which can be measured and used to determine the concentration of certain electrochemically active molecules in the working fluid.

In one embodiment, the sensor 312 requires a minimum of two electrodes 316. Materials that may be used to form the electrodes 316 include, but are not limited to, carbon, platinum, and gold. As before, metal traces may span the length of the cannula 120 to electrically connect the electrodes 316 to the control circuitry 132. The metal traces may be insulated from the environment using parylene, while the electrodes 316 of the sensor 312 may be in direct contact with the fluid at the drug target site. Alternatively, thin films or molecules may also be applied to the electrodes 316 to modify their properties and improve their detection specificity to certain molecules.

In various embodiments, the electrochemical sensor 312 is used to sense growth factors, such as vascular endothelial growth factor ("VEGF") and all the VEGF derivatives (such as VEGF A, etc.), cytokines (such as TNF Alpha), the concentration level of the drug pumped by the pump 100 or of a drug that was otherwise administered (e.g., topically), proteins, and/or sugars (such as glucose). In addition, the electrochemical sensor 312 may be employed to test ascorbic acid and oxygen levels, and/or to test the osmolarity, sugar levels, and other chemicals of the cerebral spinal fluid.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An implantable pump, comprising:
   a drug reservoir chamber and an electrolyte chamber surrounded, at least in part, by a wall comprising parylene and separated from each other by an expandable parylene diaphragm, the diaphragm forming a lower boundary of one of the chambers and an upper boundary of the other chamber, the electrolyte chamber including an electrolyte liquid therein;
   a cannula, made at least in part from parylene, for conducting liquid from the drug reservoir chamber;
   electrolysis electrodes for causing, in response to a current supplied thereto, evolution of a gas in the electrolyte chamber to thereby expand the diaphragm from a space-efficient corrugated configuration having a first surface area of contact with the electrolyte liquid to an expanded configuration having a second surface area of contact with the electrolyte liquid wherein the first surface area being greater than the second surface area, so as to force the liquid from the drug reservoir through the cannula, whereby following cessation of the current, the diaphragm recovers the space-efficient corrugated configuration and re-establishes the first surface area of contact with the electrolyte liquid without reducing a volume of the drug reservoir chamber;
   a sensor, made at least in part from parylene, for monitoring at least one of a flow rate of liquid flowing through the cannula or a pressure inside the implantable pump; and
   circuitry for adjusting delivery of the liquid through the cannula by controlling, in response to the sensor, the electrolysis electrodes so as to vary an amount of liquid forced from the drug reservoir chamber.

2. The pump of claim 1, wherein the sensor is electrically connected to the circuitry via metal lines running along the cannula.

3. The pump of claim 1, wherein the sensor is a flow sensor.

4. The pump of claim 3, wherein the flow sensor is a thermal flow sensor.

5. The pump of claim 4, wherein the flow sensor comprises a single element, physically associated with the cannula, that functions both as a heater and as a temperature sensor.

6. The pump of claim 4, wherein the flow sensor comprises a heater and a temperature sensor, both physically associated with the cannula, the temperature sensor being located downstream of the heater.

7. The pump of claim 4, wherein the flow sensor comprises a heater and first and second temperature sensors, all physically associated with the cannula, the first temperature sensor being located downstream of the heater and the second temperature sensor being located upstream of the heater.

8. The pump of claim 3, wherein the flow sensor is a time-of-flight sensor.

9. The pump of claim 8, wherein the flow sensor comprises a heater and a temperature sensor, both physically associated with the cannula, the temperature sensor being located downstream of the heater, and wherein the circuitry causes a discrete pulse of power to be applied to the heater and detection, by the temperature sensor, of liquid heated by the heater.

10. The pump of claim 9 further comprising a second temperature sensor physically associated with the cannula and located upstream of the heater.

11. The pump of claim 9 further comprising at least a second temperature sensor physically associated with the cannula and located downstream of the heater.

12. The pump of claim 8, wherein the flow sensor comprises two upstream electrodes and two downstream electrodes, each physically associated with the cannula, and wherein the circuitry causes a discrete voltage pulse to be applied across the two upstream electrodes and detection, by the two downstream electrodes, of an electrochemical pulse generated in the liquid flowing through the cannula.

13. The pump of claim 3, wherein the flow sensor comprises a pressure sensor in the reservoir.

14. The pump of claim 3, wherein the flow sensor comprises at least one pressure sensor in the cannula.

15. The pump of claim 3 further comprising a temperature sensor not in proximity to the flowing liquid for facilitating compensation for fluctuations in an ambient temperature.

16. The pump of claim 1, wherein the sensor is a pressure sensor.

17. The pump of claim 16 further comprising a check valve in the cannula, the pressure sensor being located inside the cannula and downstream of the check valve.

18. The pump of claim 16, wherein the circuitry detects a pump malfunction based on the monitored pressure.

19. The pump of claim 18, wherein the pressure sensor is placed in the drug reservoir or in proximity to an interface between the cannula and the drug reservoir.

20. The pump of claim 16 further comprising a flow sensor for monitoring a flow rate of the liquid.

21. The pump of claim 20, wherein the circuitry detects a pump malfunction based on the monitored pressure and flow.

22. The pump of claim 1, further comprising a pressure sensor located at a distal end of the cannula for measuring pressure at the target site.

23. The pump of claim 22, wherein the circuitry adjusts pump operation based on monitored pressure at the target site.

24. The pump of claim 22, wherein the pressure sensor is inside the cannula.

25. The pump of claim 22, wherein the pressure sensor is outside the cannula.

26. The pump of claim 1, wherein the circuitry is configured to adjust, based on the monitored flow rate and/or pressure, a dosing schedule and a volume of the liquid delivered by the pump.

27. The pump of claim 1, wherein the diaphragm recovers the space-efficient corrugated configuration when the gas in the electrolyte chamber condenses back into a liquid state.

* * * * *